(12) United States Patent
Liu et al.

(10) Patent No.: US 12,043,834 B2
(45) Date of Patent: Jul. 23, 2024

(54) METHOD FOR CONSTRUCTING TREHALOSE MULTI-ENZYME COMPLEX IN VITRO MEDIATED BY ARTIFICIAL SCAFFOLD PROTEIN

(71) Applicant: Qilu University of Technology, Jinan (CN)

(72) Inventors: Hongling Liu, Jinan (CN); Tengfei Wang, Jinan (CN); Ruiming Wang, Jinan (CN); Xinyi Zhang, Jinan (CN)

(73) Assignee: Qilu University of Technology, Jinan (CN)

( * ) Notice: Subject to any disclaimer, the term of this patent is extended or adjusted under 35 U.S.C. 154(b) by 90 days.

(21) Appl. No.: 17/525,283

(22) Filed: Nov. 12, 2021

(65) Prior Publication Data
US 2022/0204965 A1    Jun. 30, 2022

(30) Foreign Application Priority Data
Dec. 24, 2020 (CN) .......................... 202011551143.3

(51) Int. Cl.
| | |
|---|---|
| *C12N 15/52* | (2006.01) |
| *C12N 9/10* | (2006.01) |
| *C12N 9/26* | (2006.01) |
| *C12N 9/90* | (2006.01) |
| *C12N 11/18* | (2006.01) |
| *C12N 15/03* | (2006.01) |
| *C12N 15/75* | (2006.01) |

(52) U.S. Cl.
CPC ........... *C12N 15/52* (2013.01); *C12N 9/1051* (2013.01); *C12N 9/2408* (2013.01); *C12N 9/90* (2013.01); *C12N 11/18* (2013.01); *C12N 15/03* (2013.01); *C12N 15/75* (2013.01); *C12Y 302/01141* (2013.01); *C12Y 504/99015* (2013.01)

(58) Field of Classification Search
None
See application file for complete search history.

(56) References Cited

PUBLICATIONS

Liu, H., Yang, S., Wang, X. and Wang, T., 2019. Production of trehalose with trehalose synthase expressed and displayed on the surface of *Bacillus subtilis* spores. Microbial cell factories, 18, pp. 1-13. (Year: 2019).*

* cited by examiner

*Primary Examiner* — Neil P Hammell
*Assistant Examiner* — Khaleda B Hasan
(74) *Attorney, Agent, or Firm* — Mark C. Johnson; Johnson |Dalal

(57) ABSTRACT

The present disclosure relates to a method for constructing a trehalose polyenzyme complex in vitro by mediation of an artificial scaffold protein, which mainly comprises the following steps: constructing a recombinant bacterium WB800n-ScafCCR for self-assembled scaffold protein module; constructing a recombinant bacterium WB800n-P43-phoD -treY-Ccdoc for self-assembled catalytic module; constructing a recombinant bacterium WB800n-P43-phoD-treZ-Ctdoc for self-assembled catalytic module; constructing a recombinant bacterium WB800n-P43-phoD-cgt-Rfdoc for self-assembled catalytic module; secretorily expressing the recombinant bacteria and self-assembling in vitro to obtain a recombinant trehalose multi-enzyme complex. The trehalose multi-enzyme complex constructed by the method of the present disclosure has a higher catalytic efficiency in preparing trehalose than that of mixed free enzymes, and the method can be used for production of high quality trehalose after immobilization with cellulose microspheres.

13 Claims, 9 Drawing Sheets
Specification includes a Sequence Listing.

SEQUENCE LISTING

<160> NUMBER OF SEQ ID NOS: 26

<210> SEQ ID NO 1
<211> LENGTH: 2834
<212> TYPE: DNA
<213> ORGANISM: Artificial Sequence
<220> FEATURE:
<223> OTHER INFORMATION: Gene fragment of recombinant scaffold protein ScafCCR

<400> SEQUENCE: 1

| | | | | | |
|---|---|---|---|---|---|
| agcttcgtgc | atgcaggccg | gggcatatgg | gaaacagcgc | ggacgcagcg | gaatttccaa | 60 |
| tttcatgccg | cagccgcctg | cgctgttctc | atttgcggct | tccttgtaga | gctcagcatt | 120 |
| attgagtgga | tgattatatt | cctttttgata | ggtggtatgt | tttcgcttga | acttttaaat | 180 |
| acagccattg | aacatacggt | tgatttaata | actgacaaac | atcaccctct | tgctaaagcg | 240 |
| gccaaggacg | ctgccgccgg | ggctgttttgc | gtttttgccg | tgatttcgtg | tatcattggt | 300 |
| ttacttatttt | ttttgccaaa | gctgtaatgg | ctgaaaattc | ttacatttat | tttacatttt | 360 |
| tagaaatggg | cgtgaaaaaa | agcgcgcgat | tatgtaaaat | ataaagtgat | agcggtacca | 420 |
| ttataggtaa | gagaggaatg | tacacatgaa | cagacaagaa | ttaataacag | aagcttatgg | 480 |
| catacgacag | tcgttttgat | gaatgggtac | agaaactgaa | agaggaaagc | tttcaaaaca | 540 |
| atacgtttga | ccgccgcaaa | tttattcaag | gagcggggaa | gattgcagga | ctttctcttg | 600 |
| gattaacgat | tgcccagtcg | gttggggcct | tgaagtaat | gacaacaaca | ggcggccaga | 660 |
| caagcaatgc | ggatttaaa | tttagctttg | ttgatgataa | aggccaaagc | acagtcaacg | 720 |
| caaaagcagg | cgatgaaatt | acagtttgtg | tgcaggtaga | tgcaggaaat | aatacatgcg | 780 |
| caggcatgga | tgtacaattt | agcacaagcg | gcttagcgat | tgatgaattt | gaaaataatt | 840 |
| cagaagcatg | cggaaacgca | aaacttgcaa | aaaatgaaaa | agaactgcgc | gcaaattta | 900 |
| caagcacagg | cacagatggc | gaaccgatga | agttagcaa | tggcaaagat | gcgtttacgt | 960 |
| tttatgtgac | aattccggca | tatgccaaag | atacatatta | tgttattgga | tttgttgatt | 1020 |
| ctgaacttaa | tgtgttaaa | gaaggcggca | cgggcgataa | cacgattgcc | ttttatacac | 1080 |
| cgttaacaat | taatggaaca | ccaaacctg | gcacaacaga | tggcggagtt | aatgttggca | 1140 |
| atgcaacacc | gacaaaagga | gctacaccta | caaatacggc | tacaccaaca | aagtcagcta | 1200 |
| cagctacacc | gacaagacca | agcgtgccga | cgaacacacc | tacaaacaca | atggtgccgt | 1260 |
| cagatggagt | cgtagtagaa | attggcaaag | tgacaggatc | tgtcggaaca | acagtggaaa | 1320 |
| tcccggtcta | ttttcgtgga | gttccttcta | aaggcattgc | gaattgcgat | tttgtctttc | 1380 |
| gttatgatcc | gaacgtcctt | gaaatcattg | gaattgatcc | aggcgatatt | attgtggatc | 1440 |
| cgaacccgac | gaaaagcttt | gatacagcca | tttatccgga | tcgcaaaatc | attgtgtttt | 1500 |
| tatttgcaga | agattcagga | acaggcgcct | atgcaattac | aaaggatgga | gtgtttgcga | 1560 |
| aaattagagc | tacagttaaa | agttcagcac | ctggatatat | tacatttgac | gaagtcggcg | 1620 |
| gctttgcaga | taatgattta | gttgaacaaa | aagtgagctt | tatcgatggc | ggcgtcaatg | 1680 |
| tgggcaacgc | aacaccgaca | aaaggcgcga | cacctacaaa | tacagcaaca | ccgacgaaat | 1740 |
| ctgctacggc | aaccccgacg | aggccgagcg | tgcctacgaa | taccgacaa | atacaccgg | 1800 |
| ccaatacacc | ggttagcggc | aaccttaaag | ttgaattta | taattctaat | ccttcagata | 1860 |
| caacaaactc | aatcaaccct | caatttaaag | taacaaatac | gggaagctca | gcaattgatc | 1920 |
| tttccaaatt | gacacttaga | tactattata | cggtagatgg | ccaaaaagat | cagacatttt | 1980 |

```
ggtgtgatca tgcagcgatt attggaagca atggctcata taatggcatt acatcaaatg   2040
tcaaaggcac atttgttaaa atgtcaagct ctacaaacaa cgcggataca tatcttgaaa   2100
tctcatttac gggcggtaca cttgaaccgg agcccatgt gcaaattcag ggacgctttg    2160
caaaaaatga ttggagcaat tatacacaat ctaatgatta ttcatttaaa agcgcttctc   2220
aatttgtcga atgggatcag gttacagcat atcttaacgg agttctggtc tggggaaaag   2280
aaccgggcgg cagcgtggtc ccgagcacac aaccagtcac gacaccgccg gccacaacaa   2340
aacctccggc aacaacaaaa ccgccggcaa caacgattcc gccgagcgac gttacagtgg   2400
gaacagctaa tggaaaacca ggcgatacag ttacagttcc ggtgacgttt gcagatgttg   2460
caaaaatgaa aaatgtaggc acgtgcaatt tctatttggg ctatgatgca tcacttctgg   2520
aagtggtttc agttgatgct ggacctatcg ttaaaaatgc ggccgtgaat ttttcaagct   2580
cagctagtaa tggcacaatt agcttttctgt ttttagataa tacaattaca gatgaactta   2640
ttacagcaga tggcgttttt gctaatatta aatttaaact gaaaagcgtg acagccaaaa   2700
caacaacacc ggtcacattt aaagatggag gcgcgtttgg cgatggcaca atgagcaaaa   2760
ttgcaagcgt cacaaaaaca aatggcagcg tcacaattga tccgggcaca caacatcatc   2820
atcaccatca ttaa                                                     2834

<210> SEQ ID NO 2
<211> LENGTH: 3017
<212> TYPE: DNA
<213> ORGANISM: Artificial Sequence
<220> FEATURE:
<223> OTHER INFORMATION: Gene fragment of P43-phoD-treY-Ccdoc

<400> SEQUENCE: 2
agcttcgtgc atgcaggccg gggcatatgg gaaacagcgc ggacgcagcg gaatttccaa     60
tttcatgccg cagccgcctg cgctgttctc atttgcggct tccttgtaga gctcagcatt    120
attgagtgga tgattatatt cctttttgata ggtggtatgt tttcgcttga acttttaaat    180
acagccattg aacatacggt tgatttaata actgacaaac atcaccctct tgctaaagcg    240
gccaaggacg ctgccgccgg ggctgtttgc gttttttgccg tgatttcgtg tatcattggt    300
ttacttattt ttttgccaaa gctgtaatgg ctgaaaattc ttacatttat tttacatttt    360
tagaaatggg cgtgaaaaaa agcgcgcgat tatgtaaaat ataaagtgat agcggtacca    420
ttataggtaa gagaggaatg tacacatgaa cagacaagaa ttaataacag aagcttatgg    480
catacgacag tcgttttgat gaatgggtac agaaactgaa agaggaaagc tttcaaaaca    540
atacgtttga ccgccgcaaa tttattcaag gagcgggaa gattgcagga ctttctcttg    600
gattaacgat tgcccagtcg gttggggcct tgaagtagt gatatcagca acctacagat    660
tacagttaaa taagaatttt aattttggtg acgtaatcga taacctatgg tatttaagg    720 atttaggagt ttcccatctc tacctctctc ctgtcttaat ggcttcgcca ggaagtaacc    780
atgggtacga tgtaatagat cattcaagga taaacgatga acttggagga gagaaagaat    840
acaggagatt aatagagaca gctcatacta ttggattagg tattatacag gacatagtac    900
caaatcacat ggctgtaaat tctctaaatt ggcgactaat ggatgtatta aaaatgggta    960 aaagagtaa atattatacg tactttgact ttttcccaga agatgataag atacgattac   1020
ccatattagg agaagattta gatacagtga taagtaaagg tttattaaag atagtaaaag   1080
atggagatga atatttccta gaatatttca atggaaaact tcctctaaca gaggttgaa    1140 atgatatata cgacactttta caaaaacaga attatacccct aatgtcttgg aaaaatcctc   1200
```

-continued

```
ctagctatag acgattcttc gatgttaata ctttaatagg agtaaatgtc gaaaaagatc      1260
acgtatttca agagtcccat tcaaagatct tagatttaga tgttgatggc tatagaattg      1320
atcatattga tggattatat gatcctgaga aatatattaa tgacctgagg tcaataatta      1380
aaaataaaat aattattgta gaaaaaattc tgggatttca ggaggaatta aaattaaatt      1440
cagatggaac tacaggatat gacttcttaa attactccaa cttactgttt aattttaatc      1500
aagagataat ggacagtata tatgagaatt tcacagcgga gaaatatct ataagtgaaa       1560 gtataaagaa aataaaagcg caaataattg atgagctatt tagttatgaa gttaaaagat      1620
tagcatcaca actaggaatt agctacgata tattgagaga ttaccttct tgtatagatg       1680 tgtacagaac ttatgctaat cagattgtaa aagagtgtga taagaccaat gagatagagg      1740
aagcaaccaa aagaaatcca gaggcttata ctaaattaca acaatatatg ccagcagtat      1800
acgctaaagc ttatgaagat actttcctct ttagatacaa tagattaata tccataaatg      1860
aggttggaag cgatttacga tattataaga tatcgcctga tcagtttcat gtatttaatc      1920
aaaaacgaag aggaaaaatc acactaaatg ccactagcac acatgatact aagtttagtg      1980
aagatgtaag gatgaaaata agtgtattaa gtgaatttcc tgaagaatgg aaaaataagg      2040
tcgaggaatg gcatagtatc ataaatccaa aggtatcaag aaatgatgaa tatagatatt      2100
atcaggtttt agtgggaagt ttttatgagg gattctctaa tgattttaag gagagaataa      2160
agcaacatat gataaaaagt gtcagagaag ctaagataaa tacctcatgg agaaatcaaa      2220
taaaagaata tgaaaataga gtaatggaat tagtggaaga aacttttacc aataaggatt      2280
tcattaaaag tttcatgaaa tttgaaagta agataagaag gatagggatg attaagagct      2340
tatccttggt cgcattaaaa attatgtcag ccggtatacc tgattttat cagggaacag       2400 aaaatatggcg atatttactt acagatccag ataacagagt cccagtggat tttaagaaat      2460
tacacgaaat attagaaaaa tccaaaaaat ttgaaaaaaa tatgttagag tctatggacg      2520
atggaagaat taagatgtat ttaacatata agcttttatc cctaagaaaa cagttggctg      2580
aggatttttt aaagggcgag tataagggat tagatctaga agaaggacta tgtgggttta      2640
ttaggtttaa caaaattttg gtaataataa aaaccaaggg aagtgttaat tacaaactga      2700
aacttgaaga gggagcaatt tacacagatg tattgacagg agaagaaatt aaaaagagg       2760 tacagattaa tgagctacct aggatactag ttagaatgcc ggaccaggt ccggaaaaac        2820 tgctgggcga tgttaatggc gatgaaacag ttgatgcgat tgatctggca attctgaaaa      2880
aatatctgct taattcatca acaacaatta atacagcaaa tgcagatatg aattcagata      2940
atgcaattga tgcgattgat tatgcactgc tgaaaaaagc actgctgagc attcaacacc      3000
accaccacca ccactaa                                                    3017
```

<210> SEQ ID NO 3  
<211> LENGTH: 2558  
<212> TYPE: DNA  
<213> ORGANISM: Artificial Sequence  
<220> FEATURE:  
<223> OTHER INFORMATION: Gene fragment P43-phoD-treZ-Ctdoc

<400> SEQUENCE: 3

```
agcttcgtgc atgcaggccg gggcatatgg gaaacagcgc ggacgcagcg gaatttccaa        60
tttcatgccg cagccgcctg cgctgttctc atttgcggct tccttgtaga gctcagcatt       120
attgagtgga tgattatatt ccttttgata ggtggtatgt tttcgcttga acttttaaat       180
```

-continued

```
acagccattg aacatacggt tgatttaata actgacaaac atcaccctct tgctaaagcg    240
gccaaggacg ctgccgccgg ggctgtttgc gttttttgccg tgatttcgtg tatcattggt   300
ttacttattt ttttgccaaa gctgtaatgg ctgaaaattc ttacatttat tttacattt    360 tagaaatggg cgtgaaaaaa agcgcgcgat tatgtaaaat ataaagtgat agcggtacca   420
ttataggtaa gagaggaatg tacacatgaa cagacaagaa ttaataacag aagcttatgg   480
catacgacag tcgttttgat gaatgggtac agaaactgaa agaggaaagc tttcaaaaca   540
atacgtttga ccgccgcaaa tttattcaag gagcgcggaa gattgcagga ctttctcttg   600
gattaacgat tgcccagtcg gttggggcct ttgaagtaat gttttcgttc ggtggaaata   660
ttgaaaaaaa taaaggtatc tttaagttat gggcaccttta tgttaatagt gttaagctga   720
agttaagcaa aaaacttatt ccaatggaaa aaaacgatga gggattttttc gaagtagaaa   780 tagacgatat cgaggaaaat ttaacctatt cttatattat agaagataag agagagatac   840
ctgatcccgc atcacgatat caaccttttag gagttcatga caaatcacaa cttataagaa   900
cagattatca gattcttgac cttggaaaag taaaaataga gatctaata atatatgaac    960 tccacgttgg tactttttcc caagaaggaa atttcaaagg agtaatagaa aagttagatt   1020
acctcaagga tctaggaatc acaggaattg aactgatgcc tgtggcacaa tttccaggga   1080
atagagattg gggatacgat ggtgtttttc tatacgcagt tcaaaatact tatggcggac   1140
catgggaatt ggctaagcta gtaaacgagg cacataaaag gggaatagcc gtaattttgg   1200
atgttgtata taatcatata ggtcctgagg gaaattacct tttaggatta ggtccttatt   1260
tttcagacag atataaaact ccatggggat taacatttaa ttttgatgat aggggatgtg   1320
atcaagttag aaaattcatt ttagaaaatg tcgagtattg gtttaagacc tttaaaatcg   1380
atggtctgag actggatgca gttcatgcaa tttttgataa ttcgcctaag catatcctcc   1440
aagagatagc tgaaaaagcc catcaattag gaaaatttgt tattgctgaa agtgatttaa   1500
atgatccaaa aatagtaaaa gatgattgtg atataaaat agatgctcaa tgggttgacg   1560
atttccacca cgcagttcat gcattcataa caaaagaaaa agattattat taccaggatt   1620
ttggaaggat agaagatata gagaaaactt taaagatgtt ttttgtttat gatggaaagt   1680
attctagata cagaggaaga actcatggtg ctcctgtagg tgatcttcca ccacgtaaat   1740
ttgtagtctt catacaaaat cacgatcaag taggaaatag aggaaatggg gaaagacttt   1800
ccatattaac cgataaaacg acataccttta tggcagccac actatatata ctctcaccgt   1860
atataccgct aatatttatg ggcgaggaat attatgagac gaatccttt ttcttcttct    1920 ctgatttctc agatcccgta ttaattaagg gtgttagaga aggtagacta aaggaaaata   1980
atcaaatgat agatccacaa tctgaggaag cgttcttaaa gagtaaactt tcatggaaaa   2040
ttgatgagga agttttagat tattataaac aactgataaa tatcagaaag agatataata   2100
attgtaaaag ggtaaaggaa gttaggagag aagggaactg tattactttg atcatggaaa   2160
aaataggaat aattgcatcg tttgatgata ttgtaattaa ttctaaaatt acaggtaatt   2220
tacttatagg cataggattt ccgaaaaaat tgaaaaaga tgaattaatt aaggttaaca   2280
gaggtgttgg ggtatatcaa ttagaaacgt ataaagttcc gggcacaccg agcacaaaac   2340
tgtatggcga tgttaatgat gatggcaaag ttaatagcac agatgcagtt gcactgaaaa   2400
gatatgttct gagaagcggc attagcatta atacagataa tgcagatctg aatgaagatg   2460
gcagagttaa tagcacagat ctgggcattc tgaaagata tattctgaaa gaaattgata   2520
cactgccgta taaaaatcat catcaccatc atcattaa                           2558
```

<210> SEQ ID NO 4
<211> LENGTH: 3162
<212> TYPE: DNA
<213> ORGANISM: Artificial Sequence
<220> FEATURE:
<223> OTHER INFORMATION: Gene fragment P43-phoD-cgt-Rfdoc

<400> SEQUENCE: 4

```
agcttcgtgc atgcaggccg gggcatatgg gaaacagcgc ggacgcagcg gaatttccaa      60
tttcatgccg cagccgcctg cgctgttctc atttgcggct tccttgtaga gctcagcatt     120
attgagtgga tgattatatt ccttttgata ggtggtatgt tttcgcttga actttttaaat    180
acagccattg aacatacggt tgatttaata actgacaaac atcaccctct tgctaaagcg     240
gccaaggacg ctgccgccgg ggctgttttgc gttttttgccg tgatttcgtg tatcattggt   300
ttacttattt ttttgccaaa gctgtaatgg ctgaaaattc ttacatttat tttacatttt    360
tagaaatggg cgtgaaaaaa agcgcgcgat tatgtaaaat ataaagtgat agcggtacca     420
ttataggtaa gagaggaatg tacacatgaa cagacaagaa ttaataacag aagcttatgg     480
catacgacag tcgttttgat gaatgggtac agaaactgaa agaggaaagc tttcaaaaca     540
atacgtttga ccgccgcaaa tttattcaag gagcgggaa gattgcagga ctttctcttg     600
gattaacgat tgcccagtcg gttggggcct tgaagtaat gggatccggc gacagggaca     660
agcctggaat tcaaacgatt acataggagg tataacatga agaaatttct gaaatcgaca     720
gctgcgcttg ccctgggatt atcgctgacg ttcgggcttt tcagccctgc ccaggccgcg     780
ccggatacct cggtatccaa caagcaaaat ttcagcaccg acgtcatcta tcaaattttc     840
accgacaggt tttcggacgg caatcccgcc aacaatccga ccggcgcggc gtttgacgga     900
acctgcacga acctccggct gtattgcggc ggcgactggc agggcatcat caacaaaatc     960
aacgacggtt acctgaccgg gatgggcgtt accgccatct ggatctccca gccggtcgaa    1020
aacatctaca gcatcatcaa ttattccggc gtaaacaaca cggcctatca cggctactgg    1080
gccccgggact tcaagaagac gaatccggcc tacggcacga ttgcggactt ccagaacctg    1140
atcgccgccg cgcatgcaaa aaacatcaaa gtcattatcg actttgcccc gaaccatacg    1200
tcgcccgcct cgtccgacca gccttccttt gcggaaaacg gccggctgta cgataacggc    1260
acgctgctcg ggggatacac gaacgatacg cagaaacctgt tccaccataa cggcggcacg    1320
gacttttcca cgaccgaaaa cggcatctac aaaaacctgt acgatctcgc cgacctgaac    1380
cataacaaca gcaccgtgga cgtctacttg aaggacgcga tcaaaatgtg gctggacctc    1440
ggcatcgacg gcatccgcat ggatgcggtg aagcatatgc cgttcggctg cagaagagc     1500
tttatggctg ccgtcaacaa ctataagccg gtctttacct tcggcgaatg gttcctgggc    1560
gtaaatgaag tgagcccgga aaaccataag tttgccaacg aatccggcat gagcctgctt    1620
gatttccgtt ttgcccaaaa ggtgcggcag gtgttccggg acaacaccga caatatgtac    1680
ggcctgaagg cgatgctgga gggctccgca gccgattacg cccaggtgga tgaccaggtg    1740
acgttcatcg acaaccatga catggagcgt ttccacgcaa gcaatgcaaa ccgccggaag    1800
ctggagcaag cgcttgcgtt cacgctgacc tcgcgcggcg tccccgccat ttattacggc    1860
accgagcagt acatgtcggg cgggaccgat ccggacaacc gggcgcggat cccttccttc    1920
tccacgtcga cgaccgccta tcaggtcatt caaaagctgg cgccgctgcg caagtgcaac    1980
ccggccatcg cctacggatc gacgcaggag cgctggatca acaacgacgt gctcattta     2040
```

```
gagcgcaaat tcggcagcaa cgttgccgtc gttgccgtca accgcaattt aaacgcgccg    2100
gcttccattt cgggacttgt cacttccctg ccgcaaggca gctacaacga cgtccttggc    2160
ggccttctga acggcaacac gttatcggta ggctccggcg gggccgcctc caatttcacg    2220
cttgcggccg gcggcacggc ggtgtggcag tacaccgcgg ctacggcgac gccgaccatc    2280
gggcatgtcg ggccgatgat ggccaagccg ggcgtgacga tcacgatcga cggccgcggc    2340
ttcggctcta gcaaaggcac cgtctacttc ggtacgacgg cggtgagcgg ggcggacatc    2400
acgtcttggg aagacacgca gatcaaagtg aaaattccgg ccgtcgcagg cggcaactac    2460
aacattaaag tcgcaaacgc tgccggaacg gcaagcaatg tgtatgacaa cttcgaggta    2520
ttgtccggag accaggtcag cgtccgcttc gtggtcaaca acgcgacgac ggcccttggg    2580
caaaatgtgt acctgacggg cagtgtcagc gagctgggga actgggaccc ggcaaaagca    2640
atcgggccga tgtacaatca ggtcgtttac caatatccga actggtatta tgacgtcagc    2700
gttccggccg gcaaaacgat cgagttcaag ttttttgaaaa aacaaggctc caccgtcacg    2760
tgggaaggcg gcagcaacca caccttcacc gcgccgtcca gcggcaccgc gaccattaac    2820
gtgaattggc agccataacc ggaccagggt ccggaaaaac tgctgactgt aacaactcct    2880
cagcccggca caaagctcgt tcctacatgg ggcgatacaa actgcgacgg cgttgtaaat    2940
gttgctgacg tagtagttct taacagattc ctcaacgatc ctacatattc taacattact    3000
gatcagggta aggttaacgc agacgttgtt gatcctcagg ataagtccgg cgcagcagtt    3060
gatcctgcag gcgtaaagct cacagtagct gactctgagg caatcctcaa ggctatcgtt    3120
gaactcatca cacttcctca gcaccaccac caccaccact aa                      3162
```

<210> SEQ ID NO 5
<211> LENGTH: 3667
<212> TYPE: DNA
<213> ORGANISM: Artificial Sequence
<220> FEATURE:
<223> OTHER INFORMATION: Gene fragment of P43-phoD-Bscgt-Rfdoc

<400> SEQUENCE: 5

```
agcttcgtgc atgcaggccg gggcatatgg gaaacagcgc ggacgcagcg gaatttccaa      60
tttcatgccg cagccgcctg cgctgttctc atttgcggct tccttgtaga gctcagcatt     120
attgagtgga tgattatatt cctttttgata ggtggtatgt tttcgcttga acttttaaat    180
acagccattg aacatacggt tgatttaata actgacaaac atcaccctct tgctaaagcg    240
gccaaggacg ctgccgccgg ggctgtttgc gttttttgccg tgatttcgtg tatcattggt    300 tttacttattt ttttgccaaa gctgtaatgg ctgaaaattc ttacatttat tttacatttt    360
tagaaatggg cgtgaaaaaa agcgcgcgat tatgtaaaat ataaagtgat agcggtacca    420
ttataggtaa gagaggaatg tacacatgaa cagacaagaa ttaataacag aagcttatgg    480
catacgacag tcgttttgat gaatgggtac agaaactgaa agaggaaagc tttcaaaaca    540
atacgtttga ccgccgcaaa tttattcaag gagcggggaa gattgcagga ctttctcttg    600
gattaacgat tgcccagtcg gttggggcct ttgaagtaat gtctagattg atcaaccagt    660
gctacataaa ttgttttaaa cgtatttttta gtcctaacga cctatttacg aacacagtgt    720
ccataagata ttaataaatg aacagcatat tttcaccaat ttaagggcaa tgcttttggt    780
tttttacaaa caaccccgtc tttttatttta aaaggcgggg ttgttttgtt ttatatacgt    840
tttatcacaa tttgttgaag gaggaataga gttgaacgat ttaaatgatt ttttgaaaac    900
gatttcatta agctttatct ttttcttgct tctttctttta cctactgttg cggaggctga    960
```

```
cgtaacaaac aaagtcaatt actcaaaaga tgtgatttac caggttgtta ccgatcgatt   1020
ctctgacggg aatcctggca acaatccttc aggcgctatc tttagtcaaa actgtataga   1080
tcttcataag tattgtggtg gggactggca agggattata gacaaaatca atgacggtta   1140
cttaactgat ttaggcatta cggcactatg gatttctcag ccagtcgaaa acgtttatgc   1200
cctacaccca agcggctata cctcctacca tggatattgg gctcgagatt acaaaaagac   1260
aaacccttac tatgggaatt ttgatgactt tgatcgttta atgagtaccg cacatagcaa   1320
tgggataaag gtaatcatgg atttcacgcc aaatcattca tcaccggcac ttgaaacgaa   1380
ccctaactat gttgaaaatg gggcgatata tgataatggc acattattag gtaactattc   1440
aaatgatcaa caaaacctct ttcaccacaa tggcggaaca gatttctctt catatgaaga   1500
tagcatttac agaaacttat atgatctggc agactatgat ttaaacaaca cagtcatgga   1560
tcaatattta aaagagtcga ttaagttctg gttagataaa gggattgatg cattcgagt    1620 agatgccgtt aagcatatgt cagaaggtgt gcaaacctct ttaatgagcg aaatctattc   1680
gcataaacct gttttcacat ttggagaatg gtttttagga tcaggagaag ttgatcccca   1740
aaatcatcac ttcgctaatg aaagtggtat gagtttatta gatttccaat tcggtcaaac   1800
cattcgtaac gtcttaaaag atcgcacaag caactggtat gatttt aatg aaatgattac   1860 cagtacagaa aaagagtata acgaggtcat tgatcaagta accttt attg ataatcacga   1920 catgagtcgt ttttcggtag gatcatcttc aaaccgtcag acagatatgg ccctagctgt   1980
cttgcttact tctcgtggtg taccaacgat ttactacggg acagagcagt atgtaacagg   2040
tggcaacgac cctgaaaatc gcaaaccatt gaaaacattt gatcggtcta ccaactccta   2100
tcaaatcatc agtaaacttg cttcactacg ccaaacaaat tccgccttag gctatggcac   2160
tacaactgaa cgttggctga acgaagacat ttatatttat gaaagaacgt ttggcaatag   2220
tattgtatta actgctgtaa atagcagtaa tagtaaccag acgatcacta atttaaacac   2280
ctctttacct caagggaact atacagatga actacagcaa cgtttagatg gaaacacgat   2340
tactgttaac gccaatggag ccgtaaaatt cttt caatta cgagcaaata gcgtagcggt   2400
ttggcaagta agcaacccct ctacgtctcc tctaatcggc caagtgggtc ctatgatggg   2460
taagtccggg aataccataa cagtaagcgg tgaaggattt ggtgatgaga gaggaagcgt   2520
tctctttgat tcaacctctt ctgaaattat ttcttggtca aatacagaaa taagcgtaaa   2580
ggtgcctaat gtagcaggcg gttattatga tctatccgtc gtaactgcag caaacttaaa   2640
aagccctact tacaaagagt ttgaagtatt gtcaggcaat caagtcagtg tccgctttgg   2700
tgttaacaat gccacaacga gcccaggaac caatttatat atcgttggga atgtgagcga   2760
gctggggaat tgggatgctg ataaagcaat tggacctatg tttaaccaag tgatgtacca   2820 ataccccaaca tggtactatg atattagcgt tcctgccgga aaaaaccttg aatacaaata   2880
cattaaaaaa gatcagaacg gtaacgttgt ctggcaaagt ggcaacaatc gaacctatac   2940
gtcgcctact accggaacag atacggttat gattaattgg taacgaaaga gtagatacaa   3000
cccccatttc aattgtagaa aatgggggttg attgatagag aaaatcctat aatactttcc   3060
tttctaatca aaccatttta ttgagttgcg tagatgttga taaatagttc attttgccaa   3120
aaccaattga aggaaaataa tagtacgtta caataataag tagcaattag agactctcat   3180
aaaagaggct gggacataac gaaaagtagt atttgaaaag acgaatagtc taaaatatgc   3240
tgagtagcac cgctacagga gaatccttcg ctttccaggg acacggcctc agcctcctcc   3300
```

```
gtggaaaacc gccacttcag agtcttcaga cacgtgctga tccccggacc agggtccgga    3360
aaaactgctg actgtaacaa ctcctcagcc cggcacaaag ctcgttccta catggggcga    3420
tacaaactgc gacggcgttg taaatgttgc tgacgtagta gttcttaaca gattcctcaa    3480
cgatcctaca tattctaaca ttactgatca gggtaaggtt aacgcagacg ttgttgatcc    3540
tcaggataag tccggcgcag cagttgatcc tgcaggcgta aagctcacag tagctgactc    3600
tgaggcaatc ctcaaggcta tcgttgaact catcacactt cctcagcacc accaccacca    3660
ccactaa                                                              3667
```

<210> SEQ ID NO 6
<211> LENGTH: 36
<212> TYPE: DNA
<213> ORGANISM: Artificial Sequence
<220> FEATURE:
<223> OTHER INFORMATION: Sequence of forward primer P43-F

<400> SEQUENCE: 6

```
agtgaattcg agctcagctt cgtgcatgca ggccgg                              36
```

<210> SEQ ID NO 7
<211> LENGTH: 48
<212> TYPE: DNA
<213> ORGANISM: Artificial Sequence
<220> FEATURE:
<223> OTHER INFORMATION: Sequence of reverse primer P43-R

<400> SEQUENCE: 7

```
tcaaaacgac tgtcgtatgc cataagcttc tgttattaat tcttgtct                 48
```

<210> SEQ ID NO 8
<211> LENGTH: 43
<212> TYPE: DNA
<213> ORGANISM: Artificial Sequence
<220> FEATURE:
<223> OTHER INFORMATION: Sequence of forward primer phoD-F

<400> SEQUENCE: 8

```
aataacagaa gcttatggca tacgacagtc gttttgatga atg                      43
```

<210> SEQ ID NO 9
<211> LENGTH: 32
<212> TYPE: DNA
<213> ORGANISM: Artificial Sequence
<220> FEATURE:
<223> OTHER INFORMATION: Sequence of reverse primer Scaf-phoD-R

<400> SEQUENCE: 9

```
gcctgttgtt gtcattactt caaaggcccc aa                                  32
```

<210> SEQ ID NO 10
<211> LENGTH: 33
<212> TYPE: DNA
<213> ORGANISM: Artificial Sequence
<220> FEATURE:
<223> OTHER INFORMATION: Sequence of forward primer ScafCCR-F

<400> SEQUENCE: 10

```
ggggcctttg aagtaatgac aacaacaggc ggc                                 33
```

<210> SEQ ID NO 11
<211> LENGTH: 45
<212> TYPE: DNA
<213> ORGANISM: Artificial Sequence
<220> FEATURE:
<223> OTHER INFORMATION: Sequence of reverse primer ScafCCR-R

<400> SEQUENCE: 11
cgactctaga ggatccttaa tgatggtgat gatgatgttg tgtgc          45

<210> SEQ ID NO 12
<211> LENGTH: 31
<212> TYPE: DNA
<213> ORGANISM: Artificial Sequence
<220> FEATURE:
<223> OTHER INFORMATION: Sequence of reverse primer phoD-R

<400> SEQUENCE: 12
ggttgctgat atcactactt caaaggcccc a          31

<210> SEQ ID NO 13
<211> LENGTH: 37
<212> TYPE: DNA
<213> ORGANISM: Artificial Sequence
<220> FEATURE:
<223> OTHER INFORMATION: Sequence of forward primer Sase-F

<400> SEQUENCE: 13
ggttggggcc tttgaagtag tgatatcagc aacctac          37

<210> SEQ ID NO 14
<211> LENGTH: 64
<212> TYPE: DNA
<213> ORGANISM: Artificial Sequence
<220> FEATURE:
<223> OTHER INFORMATION: Sequence of reverse primer Sase-R

<400> SEQUENCE: 14
atcgccatta acatcgccca gcagttttc cggaccctgg tccggcattc taactagtat          60
ccta          64

<210> SEQ ID NO 15
<211> LENGTH: 66
<212> TYPE: DNA
<213> ORGANISM: Artificial Sequence
<220> FEATURE:
<223> OTHER INFORMATION: Sequence of forward primer ccdoc-F

<400> SEQUENCE: 15
tactagttag aatgccggac cagggtccgg aaaaactgct gggcgatgtt aatggcgatg          60
aaacag          66

<210> SEQ ID NO 16
<211> LENGTH: 61
<212> TYPE: DNA
<213> ORGANISM: Artificial Sequence
<220> FEATURE:
<223> OTHER INFORMATION: Sequence of reverse primer ccdoc-R

<400> SEQUENCE: 16
gactctagag gatccttagt ggtggtggtg gtggtgttga atgctcagca gtgctttttt          60
c          61

<210> SEQ ID NO 17
<211> LENGTH: 44
<212> TYPE: DNA
<213> ORGANISM: Artificial Sequence
<220> FEATURE:

```
<223> OTHER INFORMATION: Sequence of forward primer phoD-Hase-F

<400> SEQUENCE: 17
gaattaataa cagaagctta tgcatacga cagtcgtttt gatg                    44

<210> SEQ ID NO 18
<211> LENGTH: 44
<212> TYPE: DNA
<213> ORGANISM: Artificial Sequence
<220> FEATURE:
<223> OTHER INFORMATION: Sequence of reverse primer phoD-Hase-R

<400> SEQUENCE: 18
tgcccggaac tttatacgtt tctaattgat atccccaac acct                    44

<210> SEQ ID NO 19
<211> LENGTH: 46
<212> TYPE: DNA
<213> ORGANISM: Artificial Sequence
<220> FEATURE:
<223> OTHER INFORMATION: Sequence of forward primer ctdoc-F

<400> SEQUENCE: 19
gttggggtat atcaattaga aacgtataaa gttccgggca caccga                 46

<210> SEQ ID NO 20
<211> LENGTH: 45
<212> TYPE: DNA
<213> ORGANISM: Artificial Sequence
<220> FEATURE:
<223> OTHER INFORMATION: Sequence of reverse primer ctdoc-R

<400> SEQUENCE: 20
gtcgactcta gaggatcctt aatgatgatg gtgatgatga ttttt                  45

<210> SEQ ID NO 21
<211> LENGTH: 37
<212> TYPE: DNA
<213> ORGANISM: Artificial Sequence
<220> FEATURE:
<223> OTHER INFORMATION: Sequence of forward primer ctg-rfdoc-F

<400> SEQUENCE: 21
cggttggggc ctttgaagta atgggatccg gcgacag                           37

<210> SEQ ID NO 22
<211> LENGTH: 56
<212> TYPE: DNA
<213> ORGANISM: Artificial Sequence
<220> FEATURE:
<223> OTHER INFORMATION: Sequence of reverse primer ctg-rfdoc-R

<400> SEQUENCE: 22
tcgactctag aggatcctta gtggtggtgg tggtggtgct gaggaagtgt gatgag      56

<210> SEQ ID NO 23
<211> LENGTH: 42
<212> TYPE: DNA
<213> ORGANISM: Artificial Sequence
<220> FEATURE:
<223> OTHER INFORMATION: Sequence of reverse pHT01-P43-phoD-F

<400> SEQUENCE: 23
gcaccaccac caccaccact aaggatcctc tagagtcgac gt                     42
```

```
<210> SEQ ID NO 24
<211> LENGTH: 42
<212> TYPE: DNA
<213> ORGANISM: Artificial Sequence
<220> FEATURE:
<223> OTHER INFORMATION: Sequence of reverse pHT01-P43-phoD-R

<400> SEQUENCE: 24
cgccggatcc cattacttca aaggccccaa ccgactgggc aa                          42

<210> SEQ ID NO 25
<211> LENGTH: 40
<212> TYPE: DNA
<213> ORGANISM: Artificial Sequence
<220> FEATURE:
<223> OTHER INFORMATION: Forward primer for gene fragment treZ of MTHase

<400> SEQUENCE: 25
gcaaatgggt cgcggatcca tgttttcgtt cggtggaaat                             40

<210> SEQ ID NO 26
<211> LENGTH: 30
<212> TYPE: DNA
<213> ORGANISM: Artificial Sequence
<220> FEATURE:
<223> OTHER INFORMATION: Reverse primer for gene fragment treZ of MTHase

<400> SEQUENCE: 26
gtcgactcta gatcattcta attgatatac                                        30
```

METHOD FOR CONSTRUCTING TREHALOSE MULTI-ENZYME COMPLEX IN VITRO MEDIATED BY ARTIFICIAL SCAFFOLD PROTEIN

CROSS REFERENCE TO RELATED APPLICATION

This patent application claims the benefit and priority of Chinese Patent Application No. 202011551143.3 filed with China National Intellectual Property Administration on Dec. 24, 2020, the disclosure of which is incorporated by reference herein in its entirety as part of the present application.

REFERENCE TO SEQUENCE LISTING

The content of the ASCII text file of the sequence listing named "QUT_21_NPA1_SequenceListingST25" is 25,101 bytes in size and was created on Oct. 13, 2021. The sequence listing was electronically submitted via EFS-Web herewith the application, the entirety of which is incorporated herein by reference.

TECHNICAL FIELD

The disclosure belongs to the field of biotechnology and relates to a method for constructing a trehalose multi-enzyme complex in vitro mediated by artificial scaffold proteins.

BACKGROUND

Trehalose is a non-reducing disaccharide ubiquitous in nature. It is connected by glucose residues through α-1,1-glycosidic bonds. Trehalose is an excellent natural desiccant and antistaling agent, and a new type of functional oligosaccharide. Under harsh environmental conditions such as high temperature, high cold, high osmotic pressure and dry and water loss, trehalose allows for forming a unique protective film on the cell surface, which effectively protects protein molecules from inactivation and maintains the life process and biological characteristics of living organisms. This unique functional property makes trehalose an excellent active protective agent for protein drugs, enzymes, vaccines and other biological products. The special biological properties of trehalose make it widely used in the fields of food, cosmetics, medicine and agriculture.

There are several types of methods for preparing trehalose, including bacteria extraction method, fermentation broth extraction method, and enzymatic conversion method and the like. However, the primary method for large-scale trehalose production at home and abroad is the method in which malto-oligosaccharyl trehalose synthase (MTSase), malto-trehalose hydrolase oligosaccharyl (MTHase) and glucosyltransferase (CGTase) are mixed to catalyze liquefied starch (DE value 7-9) to prepare trehalose. MTSase acts on the reducing end of amylose or maltodextrin in the liquefied starch, and the α-1,4-glycosidic bond between the two glucose molecules at the reducing end is isomerized into a α-1,1-glycosidic bond to form a trehalose group. Then MTHase is used to specifically cleave α-1,4-glycosidic bonds adjacent to the trehalose group to give the free trehalose and maltooligosaccharide short of one trehalose molecule. Finally, the disproportionation reaction function of CGTase is utilized to promote the recombination among the short chain maltooligosaccharide molecules to form longer chain maltooligosaccharides, and then the longer chain maltooligosaccharides is catalyzed by MTSase and MTHase to form trehalose. This process takes places cycle by cycle, converting straight chain amylose or maltodextrin into trehalose constantly.

Cellosome is a self-assembled system of protein molecules, produced by certain anaerobic bacteria in nature. It is an extracellular protein complex dedicated to organizing and coordinating a variety of enzyme components to synergize and catalytically degrade lignocellulose (Gilmore SPal.2015) efficiently. Cellosomes are mainly composed of two parts: one is a multi-enzyme subunit containing a dockerin, which has a catalytic effect; the other is a scaffold protein containing multiple cohesins, which has an assembly function. Cellulase specifically binds to the cohesins on scaffold protein through dockerin to assemble a multi-enzyme complex of cellulase. The scaffold protein comprises one non-catalytic cellulose binding domain (CBM), and it functions by binding the multi-enzyme complex to the cellulose substrate. The method in which recombinant scaffold protein-mediated cellulase system is used to synergistically degrade lignocellulose has been extensively studied, and it turned out that is that the recombinant scaffold protein-mediated cellulase system has a higher catalytic efficiency than that of mixed free enzymes.

Chinese literature "Study of cellulose enzymes in secretory expression and high-efficiency synergy in *Bacillus subtilis*" (Zhang Wei Wei, Northwest Agriculture and Forestry University, master's thesis, April, 2018) reports that in order to explore the high-efficiency secretory expression of cellulase multi-enzyme complex in *Bacillus subtilis*, the structure of cellulosome was used, and dockersin-containing endocellulose, exonuclease and xylanase were combined with corresponding scaffold protein to construct a multi-enzyme complex of cellulase secretorily expressed by *Bacillus subtilis*. In the prior art, the specific interaction of cohesin-dockerin is mostly applied to the degradation of cellulose, and its application has not been extended to other areas of non-cellulase.

Chinese patent publication document CN111218467A (patent application number: 202010106831.2) discloses a method for constructing recombinant *Bacillus subtilis* that simultaneously secretes MTHase and MTSase, which uses a polypeptide pair spyCatcher/spyTag as a medium to construct a recombinant *Bacillus subtilis* that simultaneously secretes MTHase and MTSase. However, this patent publication does not concern the use of these three artificial scaffold protein mediated MTHase, MTSase and CGTase, or the use of solid cellulose beads to prepare in vitro multi-enzyme complex.

SUMMARY

In view of the deficiencies in the prior art, the present disclosure provides a method for constructing trehalose multi-enzyme complex mediated by in vitro artificial scaffold protein.

In the present disclosure, specific interaction mechanism between cohesin and dockerin in cellosomes is utilized. C-terminals of malto-oligosaccharyl trehalose synthase (MTSase), malto-oligosaccharyl trehalose hydrolase (MTHase) and glucosyltransferase (CGTase) are separately fused with the gene of the dockerin to construct a recombinant enzyme, and then the cohesins of corresponding type are recombined and spliced to form a scaffold protein, and a multi-enzyme complex for preparing trehalose is constructed through the one-to-one correspondence between cohesin and dockerin.

There is a class and type-specific interaction mechanism for cohesin and dockerin in the cellosomes. NCBI has published some gene sequences of dockerin and cohesin. GenBankMH049738.1 published genes of spliced scaffold protein: gene of the cellulose binding domain (CBM) of *Clostridium thermocellum* (*C. thermocellumde*), gene of the cohesion domain (Ctcoh) of *Clostridium thermocellum* (*C. thermocellum*), and gene of the cohesion domain gene (Cccoh) of *Clostridium cellulolyticum*. The use of synthetic biology technology to construct scaffold protein makes it possible to assemble a multi-enzyme system in vitro by artificial scaffold proteins.

For the construction of trehalose multi-enzyme complex secreted assembled and assembled in vitro, based on different assembling manner, in vitro multi-enzyme complexes of different proportion and different order, which may be immobilized with cellulose beads, are formed. Through screening, glucosyltransferase (GenBank: X78145.1) from *Bacillus circulans* 251 strain is selected, and CGTase is used to reduce the waste caused by the cascade catalysis of MTSase and MTHase, which greatly improves the utilization rate and the catalytic efficiency, and reduces the production costs.

The technical solution of the present disclosure is disclosed as follows.

The present discloses a method for constructing a recombinant strain for expressing self-assembled tri-enzyme complex, wherein the method comprises the following steps of:

Step 1: constructing recombinant bacteria WB800n-ScafCCR for self-assembled scaffold protein module, comprising:
  designing primers and amplifying a full-length sequence of P43 promoter and a full-length sequence of phoD signal peptide through PCR, using the genome of *Bacillus subtilis* WB800n as a template;
  designing primers and amplifying a full-length sequence Rfcoh-Ctcoh-CBM-Cccoh through PCR, using a gene sequence of ScafCCR in bacterial culture of biosynthetic ScafCCR as a template, and the gene fragment of Rfcoh-Ctcoh-CBM-Cccoh is designated as the gene fragment of scaffold protein ScafCCR;
  wherein gene sequence of ScafCCR in_the bacterial culture of ScafCCR is formed by ligating cohesins Rfcoh, Ctcoh and Cccoh, as well as a gene sequence of cellulose binding domain (CBD) to plasmid PUC57;
  and the nucleotide sequence of the gene fragment of the recombinant scaffold protein ScafCCR is set forth in SEQ ID NO: 1;
  double digesting yeast episomal plasmid pHT01 with restriction endonucleases ScaI and BamHI;
  measuring concentrations of the gene fragment of P43 promoter, the gene fragment of phoD signal peptide obtained in step (1) and the gene fragment of scaffold protein ScafCCR in step (2) and the digested pHT01 plasmid in step (3), then ligating these gene fragments by using a multi-fragment seamless cloning technology, and transforming the ligated fragments into *E. coli* DH5a competent cells, and verifying for successful transformation to obtain a plasmid pHT01-P43-phoD-ScafCCR, wherein the obtained recombinant plasmid is designated as pHT01-ScafCCR;
  transforming the recombinant plasmid pHT01-ScafCCR into bacterial cells of *Bacillus subtilis* WB800n to obtain a recombinant bacterium *Bacillus subtilis* WB800n which is designated as WB800n-ScafCCR;

Step 2: constructing recombinant bacteria WB800n-P43-phoD-treZ-Ctdoc for self-assembled catalytic module comprising steps of:
  b) amplifying a full-length sequence treY of malto-oligosaccharyl trehalose synthase (MTSase) through PCR, using the genome of *Sulfolobus acidocaldarius* having a accession number of ATCC 33909 as a template;
  c) designing primers and amplifying a gene sequence of dockerin Ccdoc through PCR, using the sequence of Ccdoc in a_biosynthetic Ccdoc bacterial culture as a template; wherein in the Ccdoc bacterial culture, the gene sequence of the dockerin Ccdoc is ligated to the plasmid PUC57;
  d) double digesting the yeast episomal plasmid pHT01 with restriction endonucleases ScaI and BamHI;
  e) measuring concentrations of the gene fragment of P43 promoter, the gene fragment of phoD signal peptide obtained in step a), the gene fragment treY of malto-oligosaccharyl trehalose synthase (MTSase) obtained in step b), the gene fragment of dockerin Ctdoc in step c) and the digested pHT01 plasmid in step d), then ligating these fragments by using a multi-fragment seamless cloning technology and transforming the resulting ligated fragments into *E. coli* DH5a competent cells, then verifying for successful transformation of the fragments to obtain a plasmid pHT01-P43-phoD-treY-Ccdoc;
  wherein the nucleotide sequence of the gene fragment of P43-phoD-treY-Cedoc is set forth in SEQ ID NO: 2.
  f) transforming the recombinant plasmid pHT01-P43-phoD-treY-Ccdoc obtained in step e) into the genome of the_bacterial cells of *Bacillus subtilis* WB800n to obtain a recombinant bacterium *Bacillus subtilis* WB800n which is designated as WB800n-P43-phoD-treY-Ccdoc;

Step 3: constructing recombinant bacteria WB800n-P43-phoD-treZ-Ctdoc for self-assembled catalytic module, comprising steps of:
  designing primers and amplifying the gene fragment of P43 promoter through PCR, using the genome of *Bacillus subtilis* WB800n as a template,
  II) designing primers and amplifying a full-length sequence treZ of phoD-malto-oligosaccharyl trehalose hydrolase (MTHase) through PCR to obtain a gene fragment phoD-treZ, using the genome of *E. coli* strain P43-phoD-MTHase constructed according to conventional techniques as a template;
  III) designing primers and amplifying a gene fragment of dockerin Ctdoc through PCR, using the sequence of Ctdoc in a biosynthetic Ctdoc bacterial culture as a template;
  wherein in the Ctdoc bacterial culture, the gene sequence of dockerin Ctdoc is litigated to the plasmid PUC57;
  IV) double digesting the yeast episomal plasmid pHT01 with restriction endonucleases ScaI and BamHI;
  V) measuring concentrations of the gene fragment of P43 promoter obtained in step I), the gene fragment of phoD-treZ obtained in step II), the gene fragment of dockerin Ctdoc in step III) and the digested pHT01 plasmid in step IV), then ligating these fragments by using a multi-fragment seamless cloning technology and transforming the ligated fragments into *E. coli* DH5a competent cells, and verifying for successful transformation of the fragments to obtain a plasmid pHT01-P43-phoD-treZ-Ctdoc;
  wherein the nucleotide sequence of the gene fragment P43-phoD-treZ-Ctdoc is set forth in SEQ ID NO: 3;

VI) transforming the recombinant plasmid pHT01-P43-phoD-treZ-Ctdoc obtained in step V) into bacterial cells of *Bacillus subtilis* WB800n to obtain a recombinant bacterium *Bacillus subtilis* WB800n, and the recombinant bacterium is designated as WB800n-P43-phoD-treZ-Ctdoc;

Step 4: constructing recombinant bacteria WB800n-P43-phoD-cgt-Rfdoc for self-assembled catalytic module, comprising:

designing primers and amplifying the gene fragment cgt-Rfdoc of cyclodextrin glycosyltransferase (CGTase)-dockerin Rfdoc through PCR, using the sequence of biosynthetic CGTase-Rfdoc bacterial culture as template;

wherein CGTase-Rfdoc in the bacterial culture is formed by ligating gene sequences of the cyclodextrin glycosyltransferase (CGTase) and the dockerin Rfdoc to the plasmid PUC57;

designing primers and amplifying the gene fragment of pHT01-P43-phoD through reverse PCR, using the WB800n-P43-phoD-treZ-Ctdoc strain obtained in step 3) as a template, measuring concentrations of the gene fragment cgt-Rfdoc obtained in step i) and the gene fragment pHT01-P43-phoD obtained in step ii), and ligating these fragments by using a single fragment seamless cloning technique and transforming the ligated fragments into *E. coli* DH5a competent cells, then verifying for successful transformation of the ligated fragments to obtain a plasmid pHT01-P43-phoD-cgt-Rfdoc;

wherein the nucleotide sequence of the gene fragment P43-phoD-cgt-Rfdoc is set forth in SEQ ID NO: 4;

transforming the recombinant plasmid pHT01-P43-phoD-cgt-Rfdoc obtained in step iii) into bacterial cells of *Bacillus subtilis* WB800n to prepare a recombinant bacterium *Bacillus subtilis* WB800n, and the recombinant bacterium is designated as WB800n-P43-phoD-CGT-Rfdoc;

secretorily expressing the recombinant bacterium WB800n-ScafCCR, WB800n-P43-phoD-treY-Ccdoc, WB800n-P43-phoD-treZ-Ctdoc, WB800n-P43-phoD-cgt-Rfdoc as constructed above, and performing self-assembling in vitro to obtain recombinant trehalose multi-enzyme complex.

In a preferred embodiment of the present disclosure, the nucleotide sequences of primers for PCR amplification of the gene fragment of P43 promoter in step (1) is as follows:

```
P43-F (SEQ ID NO: 6):
5'-AGTGAATTCGAGCTCAGCTTCGTGCATGCAGGCCGG-3'

P43-R (SEQ ID NO: 7):
5'-TCAAAACGACTGTCGTATGCCATAAGCTTCTGTTATTA

ATTCTTGTCT-3'
```

In a preferred embodiment of the present disclosure, in step (1), the nucleotide sequence of primers for PCR amplification of the gene fragment for secreting phoD signal peptide set forth below:

```
phoD-F (SEQ ID NO: 8):
5'-AATAACAGAAGCTTATGGCATACGACAGTCGTTTT

GATGAATG-3'

Scaf-phoD-R (SEQ ID NO: 9):
5'-GCCTGTTGTTGTCATTACTTCAAAGGCCCCAA-3'
```

In a preferred embodiment of the present disclosure, nucleotide sequences of primers for PCR amplification of the gene fragment of scaffold protein ScafCCR composed of Rfcoh-Ctcoh-CBM-Cccoh in step (2) is set forth as follows:

```
ScafCCR-F (SEQ ID NO: 10):
5'-GGGGCCTTTGAAGTAATGACAACAACAGGCGGC-3'

ScafCCR-R (SEQ ID NO: 11):
5'-CGACTCTAGAGGATCCTTAATGATGGTGATGATG

ATGTTGTGTGC-3'
```

In a preferred embodiment of the present disclosure, PCR amplification system used in step (1) or (2) is as follows:
2.5 μL of 10 μmol/L upstream primer, 2.5 μL of 10 μmol/L downstream primer, 2.5 μL of gene template, 2×Phanta® Max Master Mix 25 μL, ddH2O made up to 50 μL;

The amplification procedure is as follows:
denaturation at 95° C. for 3 min; denaturation at 95° C. for 15 sec, annealing at 60° C. for 15 sec, extension 30 sec/kb at 72° C., 30 cycles; extension at 72° C. for 5 min.

In the above amplification procedure, the step of extension 30 sec/kb, at 72° C. means that the rate of DNA polymerase amplification is 30 sec/kb at the temperature of 72° C. Due to different length of the gene to be amplified, 30 cycles of amplification is run, and the time for extension at 72° C. is different.

In the above amplification procedure, in step (4), the concentrations are measured by an ultra-light weight spectrophotometer.

In a preferred embodiment of the present disclosure, in step (5), screening for *Bacillus subtilis* WB800n strains integrating the plasmid comprises: coating transformants on a 100 μg/mL chloramphenicol-resistant LB plate, incubating the plate at 37ºC for 12h, and picking the transformants on the chloramphenicol-resistant LB plate with a toothpick and inoculating the transformants in a chloramphenicol-resistant LB liquid culture containing 100 μg/mL of chloramphenicol and culturing at 37ºC for 12 hours, running PCR amplification for verification using the above bacterial culture as a template, and performing agarose gel electrophoresis to obtain bands of interest (see FIG. 7), thus obtaining integrated recombinant bacteria strains.

According to a preferred embodiment of the present disclosure: the nucleotide sequence of primers for PCR amplification of the gene fragment of P43 promoter in step a) is as follows:

```
P43-F (SEQ ID NO: 6):
5'-AGTGAATTCGAGCTCAGCTTCGTGCATGCAGGC

CGG-3'

P43-R (SEQ ID NO: 7):
5'-TCAAAACGACTGTCGTATGCCATAAGCTTCTGT

TATTAATTCTTGTCT
```

In a preferred embodiment of the present disclosure, the nucleotide sequence of primers for PCR amplification of the gene fragment of phoD signal peptide in step a) is as follows:

```
phoD-F (SEQ ID NO: 8):
5'-AATAACAGAAGCTTATGGCATAC

GACAGTCGTTTTGATGAATG-3'
```

-continued

```
phoD-R (SEQ ID NO: 12):
5'-GGTTGCTGATATCACTACTTCA

AAGGCCCCA-the 3'
```

In a preferred embodiment of the present disclosure, the nucleotide sequence of primers for PCR amplification of the gene fragment treY of malto-oligosaccharyl trehalose synthase (MTSase) in step b) is as follows:

```
Sase-F (SEQ ID NO: 13):
5'-GGTTGGGGCCTTTGAAGTAGTGAT

ATCAGCAACCTAC-3'

Sase-R (SEQ ID NO: 14):
5'-ATCGCCATTAACATCGCCCAGCA

GTTTTTCCGGACCCTGGTCCGGCA

TTCTAACTAGTATCCTA-3'
```

In a preferred embodiment of the present disclosure, the nucleotide sequence of primers for PCR amplification of the gene fragment of dockerin Ccdoc in step c) is as follows:

```
ccdoc-F (SEQ ID NO: 15):
5'-TACTAGTTAGAATGCCGGACC

AGGGTCCGGAAAAACTGCTGGGCG

ATGTTAATGGCGATGAAACAG-3' ccdoc-R (SEQ ID NO: 16):
5'-GACTCTAGAGGATCCTTAGTG

GTGGTGGTGGTGGTGTTGAATGCT

CAGCAGTGCTTTTTTC-3'
```

In a preferred embodiment of the present disclosure, the PCR amplification system used in step a), b), or c) is as follows:
2.5 μL of 10 μmol/L upstream primer, 2.5 μL of 10 μmol/L downstream primer, 2.5 μL of gene template, 2×Phanta® Max Master Mix 25 μL, ddH2O made up to 50 μL;
The amplification procedure is conducted as follows:
denaturation at 95° C. for 3 min; denaturation at 95° C. for 15 sec, annealing at 60° C. for 15 sec, extension 30 sec/kb at 72° C., 30 cycles; extension at 72° C. for 5 min.
In the above amplification procedure, the step of extension 30 sec/kb, at 72° C. means that the rate of DNA polymerase amplification is 30 sec/kb at the temperature of 72° C. Due to different length of the gene to be amplified, 30 cycles of amplification is run, and the time for extension at 72° C. is different.
In step e) of the present disclosure, the concentrations are measured by an ultra-light weight spectrophotometer.
In a preferred embodiment of the present disclosure, in step f), screening for *Bacillus subtilis* WB800n strains integrating the plasmid comprises: coating transformants on a 100 μg/mL chloramphenicol-resistant LB plate, incubating the plate at 37° C. for 12h, and picking the transformants on the chloramphenicol-resistant LB plate with a toothpick and inoculating the transformants in a chloramphenicol-resistant LB liquid culture containing 100 μg/mL of chloramphenicol and culturing at 37°C for 12 hours, running PCR amplification for verification using the above bacterial culture as a template, and performing agarose gel electrophoresis to obtain bands of interest (see FIG. 7), thus obtaining integrated recombinant bacteria strains.

In a preferred embodiment of the present disclosure, the nucleotide sequence of primers for PCR amplification of the gene fragment of P43 promoter in step I) is as follows:

```
P43-F (SEQ ID NO: 6):
5'-AGTGAATTCGAGCTCAGCTTCGTGCAT

GCAGGCCGG-3'

P43-R (SEQ ID NO: 7):
5'-TCAAAACGACTGTCGTATGCCATAAGC

TTCTGTTATTAATTCTTGTCT-3'
```

In a preferred embodiment of the present disclosure, the nucleotide sequence of primers for PCR amplification of the gene fragment phoD-treZ in step II) is as follows:

```
phoD-Hase-F (SEQ ID NO: 17):
5'-GAATTAATAACAGAAGCTTATG

GCATACGACAGTCGTTTTGATG-3';

phoD-Hase-R (SEQ ID NO: 18):
5'-TGCCCGGAACTTTATACGTTTCT

AATTGATATACCCCAACACCT-3'
```

In a preferred embodiment of the present disclosure, the nucleotide sequence of primers for PCR amplification of Ctdoc gene fragment in step III) is as follows:

```
ctdoc-F (SEQ ID NO: 19):
5'-GTTGGGGTATATCAATTAGAAACG

TATAAAGTTCCGGGCACACCGA-3' ctdoc-R (SEQ ID NO: 20):
5'-GTCGACTCTAGAGGATCCTTAATG

ATGATGGTGATGATGATTTTT-3'
```

In a preferred embodiment of the present disclosure, the PCR amplification system in step I), II) or III) is as follows:
2.5 μL of 10 μmol/L upstream primer, 2.5 μL of 10 μmol/L downstream primer, 2.5 μL of gene template, 2×Phanta® Max Master Mix 25 μL, ddH2O made up to 50 μL;
The amplification procedure is conducted as follows:
denaturation at 95° C. for 3 min; denaturation at 95° C. for 15 sec, annealing at 60° C. for 15 sec, extension 30 sec/kb at 72° C., 30 cycles; extension at 72° C. for 5 min.
In the above amplification procedure, the step of extension 30 sec/kb, at 72° C. means that the rate of DNA polymerase amplification is 30 sec/kb at the temperature of 72° C. Due to different length of the gene to be amplified, 30 cycles of amplification is run, and the time for extension at 72° C. is different.
In a preferred embodiment of the present disclosure, in step V), the concentration is measured by an ultra-light weight spectrophotometer.
In a preferred embodiment of the present disclosure, in step VI), screening for *Bacillus subtilis* WB800n strains integrating the plasmid comprises: coating transformants on a 100 μg/mL chloramphenicol-resistant LB plate, incubating the plate at 37°C for 12h, and picking the transformants on the chloramphenicol-resistant LB plate with a toothpick and inoculating the transformants in a chloramphenicol-resistant LB liquid culture containing 100 μg/mL of chloramphenicol and culturing at 37°C for 12 hours, running PCR amplification for verification using the above bacterial culture as a template, and performing agarose gel electrophoresis to obtain bands of interest (see FIG. 7), thus obtaining integrated recombinant bacteria strains.

In a preferred embodiment of the present disclosure, the nucleotide sequence of primers for PCR amplification of the gene fragment cgt-Rfdoc in step i) is as follows:

```
cgt-rfdoc-F (SEQ ID NO: 21):
5'-CGGTTGGGGCCTTTGAAGTAATGGGATCCGGCGACAG-3' cgt-rfdoc-R (SEQ ID NO: 22):
5'-TCGACTCTAGAGGATCCTTAGTGGTGGTGGTGGTGCT

GAGGAAGTGTGATGAG-3'
```

In a preferred embodiment of the present disclosure, the nucleotide sequence of primers for PCR amplification of the gene fragment of pHT01-P43-phoD in step ii) is as follows:

```
pHT01-P43-phoD-F (SEQ ID NO: 23):
5'-GCACCACCACCACCACCACTAAGGATCCTCTAGAGTCGACGT-3';

pHT01-P43-phoD-R (SEQ ID NO: 24):
5'-CGCCGGATCCCATTACTTCAAAGGCCCCAACCGACTGGGCAA-3'
```

In a preferred embodiment of the present disclosure, the PCR amplification system used in step i) or ii) is as follows:
2.5 μL of 10 μmol/L upstream primer, 2.5 μL of 10 μmol/L downstream primer, 2.5 μL of gene template, 2×Phanta® Max Master Mix 25 μL, ddH2O made up to 50 μL.

The amplification procedure is conducted as follows:
denaturation at 95° C. for 3 min; denaturation at 95° C. for 15 sec, annealing at 60° C. for 15 sec, extension 30 sec/kb at 72° C., 30 cycles; extension at 72° C. for 5 min.

In the above amplification procedure, the step of extension 30 sec/kb, at 72° C. means that the rate of DNA polymerase amplification is 30 sec/kb at the temperature of 72° C. Due to different length of the gene to be amplified, 30 cycles of amplification is run, and the time for extension at 72° C. is different.

In a preferred embodiment of the present disclosure step iii), the concentrations are measured by an ultra-light weight spectrophotometer.

In a preferred embodiment of the present disclosure, in step vi), screening for *Bacillus subtilis* WB800n strains integrating the plasmid comprises: coating transformants on a 100 μg/mL chloramphenicol-resistant LB plate, incubating the plate at 37° C. for 12h, and picking the transformants on the chloramphenicol-resistant LB plate with a toothpick and inoculating the transformants in a chloramphenicol-resistant LB liquid culture containing 100 μg/mL of chloramphenicol and culturing at 37°C for 12 hours, running PCR amplification for verification using the above bacterial culture as a template, and performing agarose gel electrophoresis to obtain bands of interest (see FIG. 7), thus obtaining integrated recombinant bacteria strains.

This application further discloses the use of the above-mentioned recombinant bacteria in production of trehalose.

In a preferred embodiment of the present disclosure, the use of the recombinant bacteria in production of trehalose comprises steps of:

subjecting the engineered strains of *Bacillus subtilis* WB800n-P43-phoD-treY-Ccdoc, WB800n-P43-phoD-treZ-Ctdoc, WB800n-P43-phoD-cgt-Rfdoc, WB800n-ScafCCR to activation culturing and scaling-up culturing, respectively, fermenting the strains at 35-38° C. for 40-50 h, and using the resulting fermentation broth as a crude enzyme solution;

recovering the crude enzyme solution of scaffold protein for the strain WB800n-ScafCCR in step (i) by using cellulose beads;

mixing the crude enzyme solution of the scaffold protein recovered in step (ii) with crude enzyme solutions of the strains WB800n-P43-phoD-treY-Ccdoc, WB800n-P43-phoD-treZ-Ctdoc, and WB800n-P43-phoD-cgt-Rfdoc from step (i) at 30-70° C. and pH 4.0-8.0;

separating the cellulose beads from the resulting mixed solution in step (iii) by filtration, washing the cellulose beads thoroughly and recovering the cellulose beads after drying;

using the cellulose beads prepared in step (iv) to prepare trehalose through catalysis.

In a preferred embodiment of the present disclosure, in step (i), the activation culturing is conducted for 12 hours under the conditions of 35° C.-38° C., 180-220 rpm, and the medium used in the activation culturing is an LB liquid culture medium, and LB liquid culture medium includes the following components:

10 g/L peptone, 5 g/L yeast extract, 10 g/L NaCl, pH 7.0.

In a preferred embodiment of the present disclosure said step (i), the scale-up culturing is conducted for 12 hours under the conditions of 35° C.-38° C., 180-220 rpm, and the culture medium used in the scale-up culturing is a TB culture medium comprising the following components:

15 mL/L of glycerol, 12 g/L of tryptone, 24 g/L of yeast extract powder, 2.5 g/L of $MgCl_2$, 17 mM of $KH_2PO_4$, 72 mM of $K_2HPO_4$.

In a preferred embodiment of the present disclosure, when preparing cellulose beads in step (ii), reference was made to Li Bingjie's master's degree thesis of South China University of Technology: *Preparation of Composite Chitosan Cellulose Microspheres and Research on its Adsorption Properties*, which used the ionic liquid 1-ethyl-3-methylimidazole acetate ([EMIM]Ac) to dissolve cellulose and prepared a solution having a concentration of 3%. The cellulose was completely dissolved in a constant temperature pot at 80° C., and remained uniform magnetical stirring during dissolution of the cellulose, until a transparent liquid was obtained. Then anhydrous ethanol was used as a coagulation bath, and composite microspheres were prepared by using a squeezing method, and finally washed with deionized water 3 times to give wet cellulose beads.

In a preferred embodiment of the present disclosure, in step (iv), the drying is conducted under the conditions of a cold trap temperature of −54° C. and a vacuum degree of 8 Pa.

Three enzymes are assembled in vitro by artificial scaffolds to prepare trehalose. By inserting gene of the P43 promoter, gene of the phoD signal peptide and the gene of the malto-oligosaccharyl trehalose synthase (MTSase) treY/gene of malto-oligosaccharyl trehalose hydrolase (MTHase) treZ/gene of glucosyltransferase (CGTase) cgt gene and gene fragment Ccdoc/ctdoc/rfdoc of the dockerin into the plasmid pHT01 to construct recombinant expression plasmids pHT01-P43-phoD-treY-Ccdoc, pHT01-P43-phoD-treZ-ctdoc, and pHT01-P43-phoD-cgt-rfdoc. And a His purification tag is added to the C-terminal, and then is transformed into *Bacillus subtilis* WB800n to express the fusion enzymes MTSase-CcDoc, MTHase-CtDoc and CGTase-RfDoc. By inserting gene of the P43 promoter, the gene of phoD signal peptide, and the genes of the cohesins Cccoh, Ctcoh, Rfcoh (including a linker sequence) specifically binding to the dockerins Ccdoc, ctdoc, and rfdoc gene binding, a recombinant expression plasmid pHT01-scafCCR is constructed. A combination of a CBM gene and a cohesin gene is connected at the 5'-end of the recombinant expression plasmid pHT01-scafCCR, and a terminal His purification tag is added to the terminal. The resulting plasmid pHT01-scafCCR is transformed into *Bacillus subtilis* WB800n for secretory expression, and finally fusion enzyme and the scaffold protein self-assemble in vitro to obtain the recombinant trehalose multi-enzyme complex.

Beneficial effects of the technical solution of the present disclosure include:

In the present disclosure, it is for the first time to prepare trehalose by mediating three enzymes with artificial scaffold proteins, wherein the trehalose of malto-oligosaccharyl trehalose synthase (MTSase), malto-oligosaccharyl trehalose hydrolase (MTHase) and glucosyltransferase (CGTase) that catalyze the liquefied starch solution to prepare the trehalose are the key enzyme for catalysis. Through fusion expression of an artificial scaffold protein containing CBM, it is possible to mediate the construction of the trehalose complex multi-enzyme. It was found in the present disclosure that the efficiency in the preparation of trehalose through catalysis by the trehalose multi-enzyme complex prepared was higher than the catalytic efficiency of the mixed free enzymes. And the catalytic efficiency can be further improved by adjusting the stoichiometric ratio of the multi-enzyme system.

The artificial scaffold proteins construction according to the present disclosure mediate three enzymes to prepare trehalose, allowing for the use of the immobilized cellulose microspheres to produce high quality trehalose.

The artificial scaffold protein constructed in the present disclosure does not affect the initial enzymatic activity of malto-oligosaccharyl trehalose synthase (MTSase), malto-oligosaccharyl trehalose hydrolase (MTHase) and glucosyltransferase (CGTase), while it improves the enzymatic properties of the three enzymes, increases the temperature resistance and acid resistance, and improves the efficiency of preparation of trehalose through catalysiss.

DETAILED DESCRIPTION OF THE EMBODIMENTS

The technical solution of the present disclosure will be further described below in conjunction with the embodiments. However, the protection scope of the present disclosure is not limited to these embodiments. The reagents and drugs involved in the examples are common commercial products unless otherwise specified; the experimental operations involved in the examples are routine operations in the field unless otherwise specified.

Source of Biological Materials:

*Bacillus subtilis* WB800N was purchased from Hangzhou BIO SCI Biotechnology Co., Ltd.;

yeast episomal plasmid pHT01 was purchased from UNIBIO Biotechnology Co., Ltd.;

*Sulfolobus acidocaldarius* was deposit in the laboratory with the accession number of ATCC 33909;

Sase2-Ccdoc bacterial culture was purchased from Shanghai Sangon Biotech Company;

*E. coli* strain P43-phoD-MTHase is constructed according to conventional techniques.

In one method, the construction of P43-phoD-MTHase comprises the following steps:

designing primers and amplifying a gene fragment of P43 promoter and a gene fragment of phoD signal peptide through PCR, using a gene of *Bacillus subtilis* WB800n as a template; and the primers are:

```
P43-F (SEQ ID NO: 6):
5'-AGTGAATTCGAGCTCAGCTTCGTGCATGCAGGCCGG-3';

P43-R (SEQ ID NO: 7):
5'-TCAAAACGACTGTCGTATGCCATAAGCTTCTGTTATTA
ATTCTTGTCT-3' phoD-Hase-F (SEQ ID NO: 17):
5'-GAATTAATAACAGAAGCTTATGGCATACGACAGTCGTTT
TGATG-3';

phoD-Hase-R (SEQ ID NO: 18):
5'-TGCCCGGAACTTTATACGTTTCTAATTGATATACCCCA
ACACCT-3';
``` amplifying a gene fragment treZ of malto-oligosaccharyl trehalose hydrolase (MTHase) through PCR, using the genome of *Sulfolobus acidocaldarius* having a accession number of ATCC 33909 as a template, and the primers are:

```
treZ-F (SEQ ID NO: 25):
5'-GCAAATGGGTCGCGGATCCATGTTTTCGTTCGGTGGAAAT-3'
```

```
treZ-R (SEQ ID NO: 26):
5'-GTCGACTCTAGATCATTCTAATTGATATAC-3';
``` ligating these fragments by using a multi-fragment seamless cloning technology and transforming the ligated fragments into *E. coli* DH5α competent cells, and verifying for successful transformation of the fragments to obtain an *E. coli* strain P43-phoD-MTHase.

Hase2-Ctdoc bacterial culture was purchased from Shanghai Sangon Biotech Company;

CGTase-rfdoc bacterial culture was purchased from Shanghai Sangon Biotech Company.

ScafCCR bacterial culture was purchased from Shanghai Sangon Biotech Company;

*E. coli* DH5a was stocked in the laboratory, and it could be also commercial products.

Example 1

Figure 5:
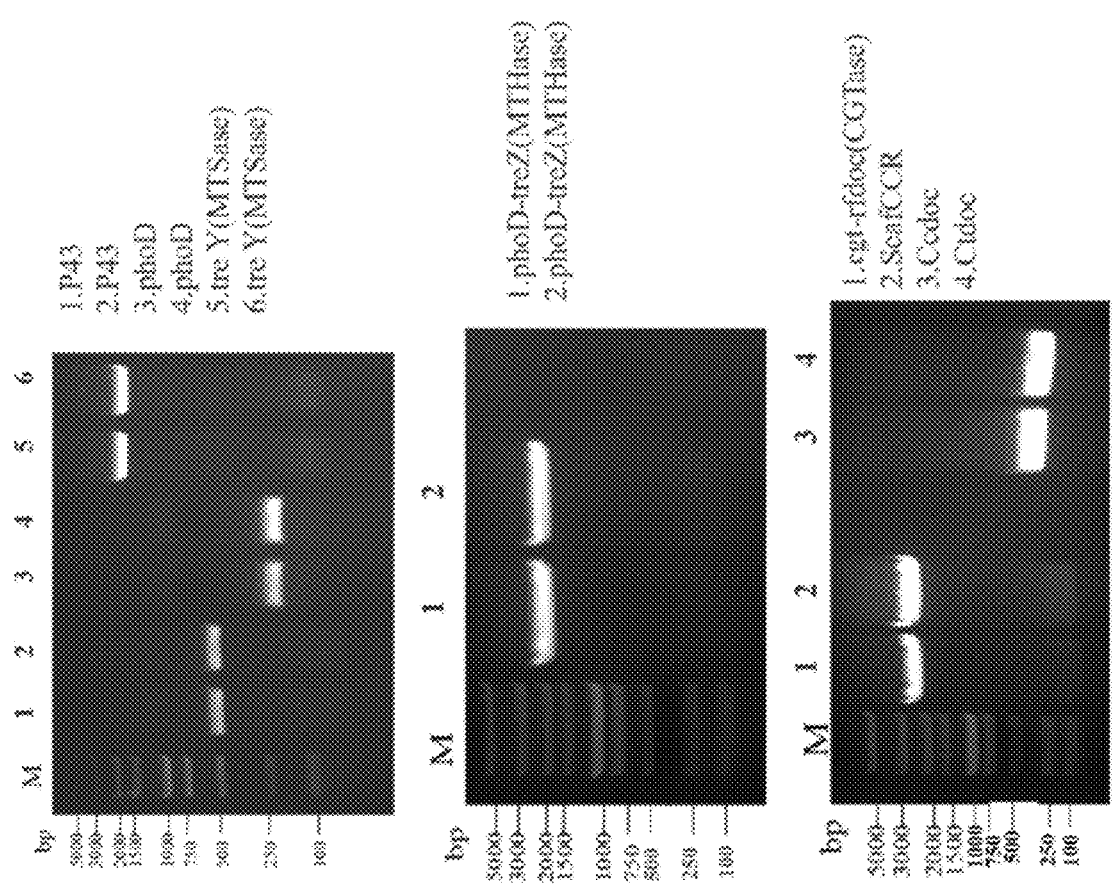
FIG. 5 shows the agarose gel electrophoresis diagrams for the P43 promoter, the gene of the phoD signal peptide, the gene of the scaffold ScafCCR gene, and the genes of dockerin Ctdoc and Ccdoc, as well as the agarose gel electrophoresis diagrams for the gene treY of the malto-oligosaccharyl trehalose synthase (MTSase), the gene phoD-treZ of malto-oligosaccharyl trehalose hydrolase (MTHase) and the gene cgt-rfdoc of the glucosyltransferase (CGTase).

Construction of Recombinant Bacteria WB800n-ScafCCR
Preparation of Gene Fragment of ScafCCR by Cloning The bacterial culture of ScafCCR synthesized by Shanghai Sangon Biotech Company was used as a template, primers were designed to amplify the gene fragment of Rfcoh-Ctcoh-CBM-Cccoh through PCR: the gene of *Bacillus subtilis* WB800n was used as a template, primers were designed to amplify the gene fragment of P43 promoter and the gene fragment of phoD signal peptide through PCR, and gel electrophoresis diagrams are shown in FIG. 5.

The primers for PCR of the gene sequence of the ScafCCR protein I set forth as follows:

```
ScafCCR-F (SEQ ID NO: 10):
5'-GGGGCCTTTGAAGTAATGACAACAACAGGCGGC-3'

ScafCCR-R (SEQ ID NO: 11):
5'-CGACTCTAGAGGATCCTTAATGATGGTGATGAT

GATGTTGTGTGC-3'
```

The PCR reaction system was as follows:

25 μL of 2×Phanta® Max Master Mix, 2.5 μL of 10 μmol/L upstream primer ScafCCR-F, 2.5 μL of 10 μmol/L downstream primer ScafCCR-R, 2.5 μL of template, ddH2O made up to 50 μL;

The above PCR reaction was carried out according to the following procedure:

denaturation at 95° C. for 3 min; denaturation at 95° C. for 15 s, annealing at 60° C. for 1 min 10 s, extension at 72° C. for 15 s, 30 cycles; extension at 72° C. for 5 min; and storage at 4° C.

After PCR was completed, the length of the fragment was analyzed with 1% agarose gel electrophoresis, the target bands were cut based on the size of the fragment, and the gel was recovered using the Shanghai Sangon Biotech Company Gel Recovery Kit.

The primers for PCR of the gene sequence of P43 promoter were as follows:

```
P43-F (SEQ ID NO: 6):
5'-AGTGAATTCGAGCTCAGCT

TCGTGCATGCAGGCCGG-3'

P43-R (SEQ ID NO: 7):
5'-TCAAAACGACTGTCGTATGCCATAAGCTTCTGTT

ATTAATTCTTGTCT-3'
```

The PCR reaction system was as follows:

25 μL of 2×Phanta® Max Master Mix, 2.5 μL of 10 μmol/L upstream primer P43-F, 2.5 μL of 10 μmol/L downstream primer P43-R, 2.5 μL of template, ddH2O made up to 50 μL.

The above PCR reaction was carried out according to the following procedure:

denaturation at 95° C. for 3 min; denaturation at 95° C. for 15 s, annealing at 60° C. for 15 s, extension at 72° C. for 15 s, 30 cycles; extension at 72° C. for 5 min; and storage at 4° C.

The primers for PCR amplification of the gene sequence of the phoD signal peptide of were as follows:

```
F-phoD (SEQ ID NO: 8):
5'-AATAACAGAAGCTTATGGCATACGACA

GTCGTTTTGATGAATG-3'

Scaf-phoD-R (SEQ ID NO: 9):
5'-GCCTGTTGTTGTCATTACTTCAAAGGCCCCAA-3'
```

The PCR reaction system was as follows:

25 μL of 2×Phanta@ Max Master Mix, 2.5 μL of 10 μmol/L upstream primer phoD-F, 2.5 μL of 10 μmol/L downstream primer phoD-R, 2.5 μL of template, ddH2O made up to 50 μL;

The above PCR reaction was carried out according to the following procedure:

denaturation at 95° C. for 3 min; denaturation at 95° C. for 15 s, annealing at 60° C. for 10 s, extension at 72° C. for 15 s, 30 cycles; extension at 72° C. for 5 min; and storage at 4° C.

double digestion of the yeast episomal plasmid pHT01 by ScaI and BamHI

The digestion system for plasmid pHT01 included:

Sixteen (16) L of plasmid pHT01; 1 μL of ScaI; 1 μL of BamHI; 2.5 μL of 10×buffer; 4.5 μL of ddH$_2$O.

Reaction conditions: reaction in a metal bath at 37° C. for 2 h.

The product from double digestion of the plasmid was detected by 1% agarose gel electrophoresis and recovered using a DNA gel recovery kit.

Figure 4:
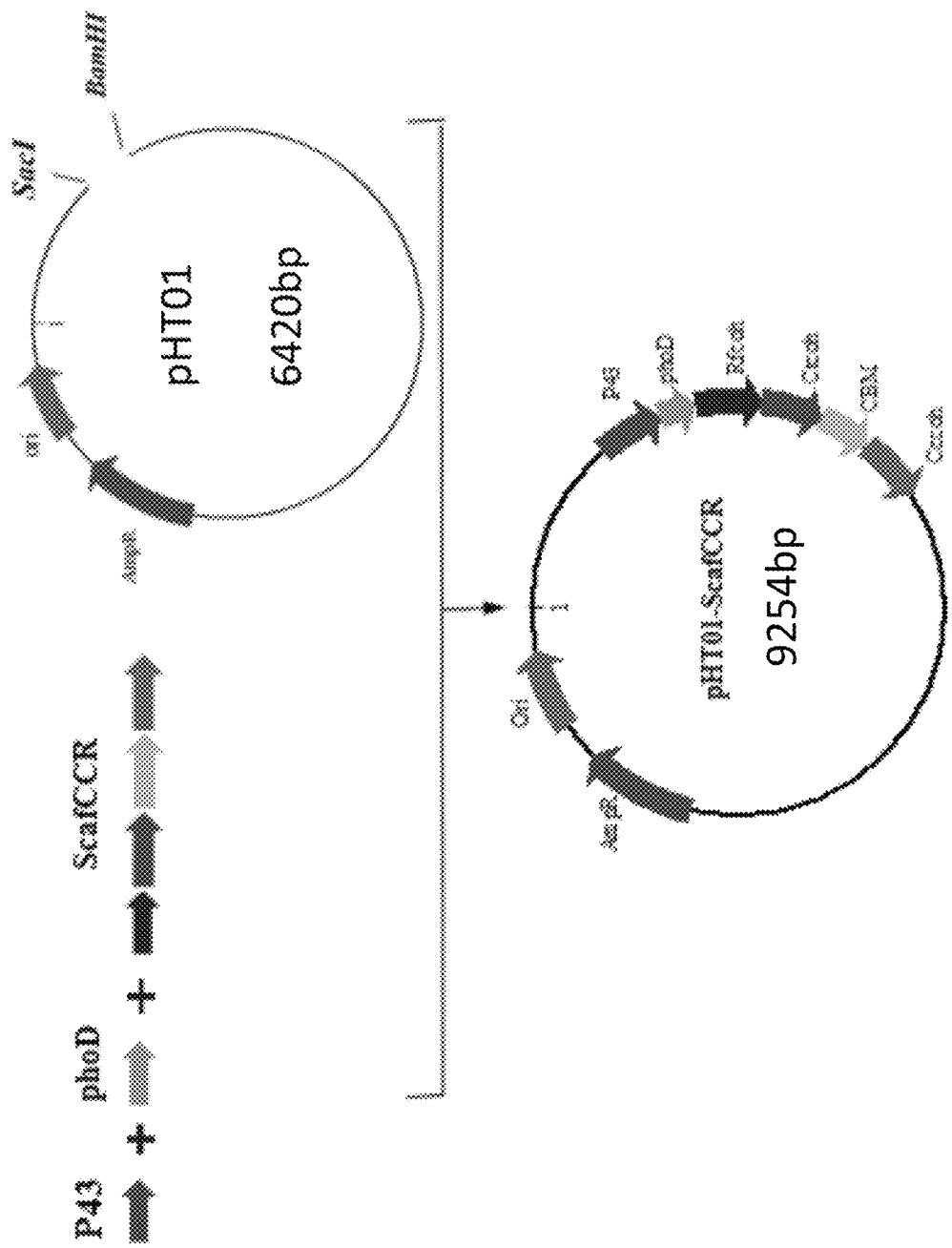
FIG. 4 is a schematic diagram of construction of vector pHT01-scafCCR.

Measurement by using an ultra-light weight spectrophotometer (MD2000H): gene fragment of the P43 promoter, gene fragment of the phoD signal peptide, gene fragment of the ScafCCR obtained from step 1) and the double digested pHT01 plasmid recovered from step (2) were measured for the concentrations, seamless cloning and ligation of multiple fragments were performed, and the fragments were transformed into *E. coli* DH5a competent cells. After the identification of successful transformation and sequencing for correctness, the prepared recombinant vector was designated as pHT01-ScafCCR. After testing, a vector pHT01-ScafCCR containing a fusion gene consisting of the gene of P43 promoter, the gene of phoD signal peptide gene and the gene ScafCCR was obtained, and the nucleotide sequence of the gene fragment of ScafCCR was set forth in SEQ ID NO: 1, and the schematic diagram for vector construction is shown in FIG. 4.

The seamless cloning and ligation system included:

160 ng of pHT01 plasmid; 120 ng of P43; 120 ng of phoD; 120 ng of ScafCCR; 2 μL of Exnase; 4 μL of 5×CEbuffer; ddH$_2$O made up to 20 μL.

Reaction conditions: reaction in a metal bath at 37° C. for 30 minutes.

Figure 6:
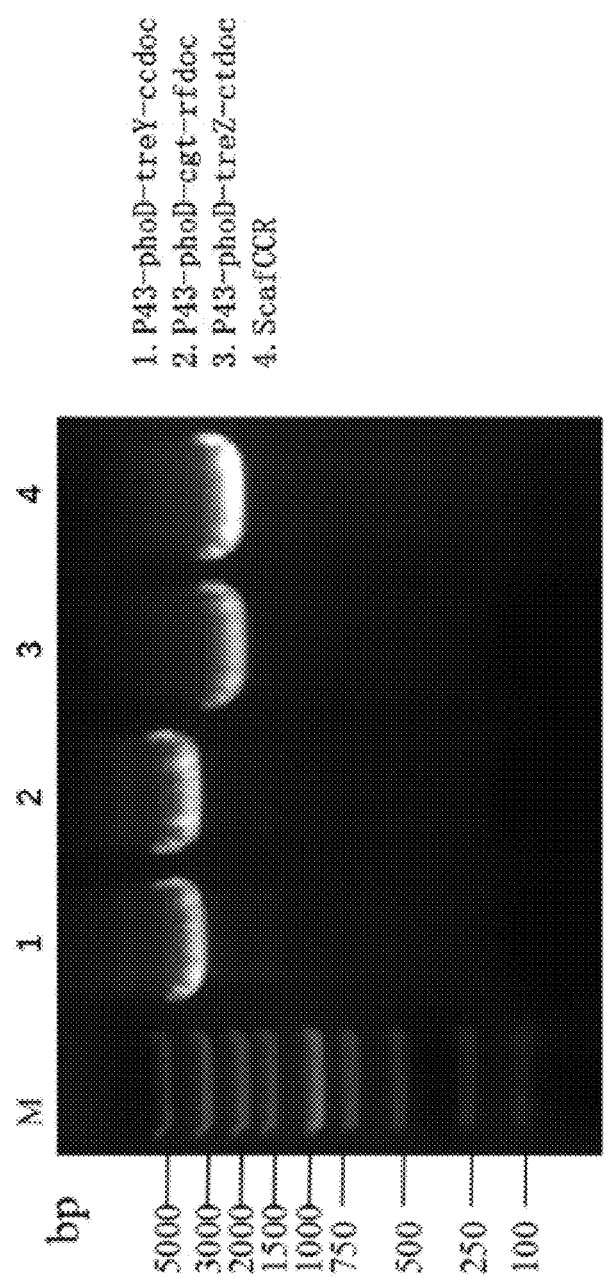
FIG. 6 is the agarose gel electrophoresis diagram of the multi-fragment cloned genes P43-phoD-tre Y-Ccdoc, P43-phoD-treZ-ctdoc, P43-phoD-cgt-rfdoc, and scafCCR.

The ligation product from seamless cloning and ligation was transformed into *E. coli* DH5α competent cells, and the agarose gel electrophoresis diagram for verification of ScafCCR is shown in FIG. 6.

Preparation of Electroporation Competent Cells of *Bacillus subtilis* WB800n

A single colony of *Bacillus subtilis* WB800n on the surface of fresh LB solid culture medium was picked and placed in 5 mL of LB culture medium and cultured overnight. 1 mL of the overnight culture was inoculated into 50 mL of GM medium (LB+0.5M sorbitol) and cultured with shaking at 37° C. until the OD600 was 1.0. The bacterial culture was placed in an ice-water bath and centrifuged at 5000 rpm for 10 minutes and at 4° C. for 8 minutes. And the bacterial cells were collected. The bacterial cells was re-suspended in 20 mL of pre-cooled ETM culture medium (0.5M sorbitol+0.5M mannitol+10% glycerol), centrifuged at 5000 rpm, 4° C. for 8 min, and the supernatant was removed, and bacterial cells were washed as such 3 times. The washed bacterial cells was re-suspended in 500 μL of ETM culture medium, and dispensed in EP tubes, with 60 μL in each tube.

Transformation of the Recombinant Plasmid pHT01-ScafCCR into *Bacillus subtilis* WB800n 5 μL of recombinant plasmid pHT01-ScafCCR was added to 50 μL competent cells WB800n, incubated on ice for 5 min, added to a pre-chilled electroporation cuvette (2 mm), and electroporation was conducted at 2500V for 5 ms. After the electric shock was finished, 1 mL of RM culture medium (LB+0.5M sorbitol+0.38M mannitol) preheated at 37° C. was added immediately into the electroporation cuvette, shaken and resuscitated at 37° C. for 3 h, and spread on the LB plate containing 100 μg/mL of chloramphenicol for inverted culturing at 37° C. to screen for chloramphenicol-resistant strains.

Identification of Medium Containing Positive Recombinant Bacteria WB800n

The above-described positive recombinant bacteria colonies were inoculated into an LB liquid culture medium (containing 100 μg/mL of chloramphenicol) were cultured overnight. Kits from Shanghai Sangon Biotech Company were used to extract the genomic DNA, the obtained genomic DNA was used as a template, and P43-F and ScafCCR-R were used as the primers for PCR amplification.

Figure 7:
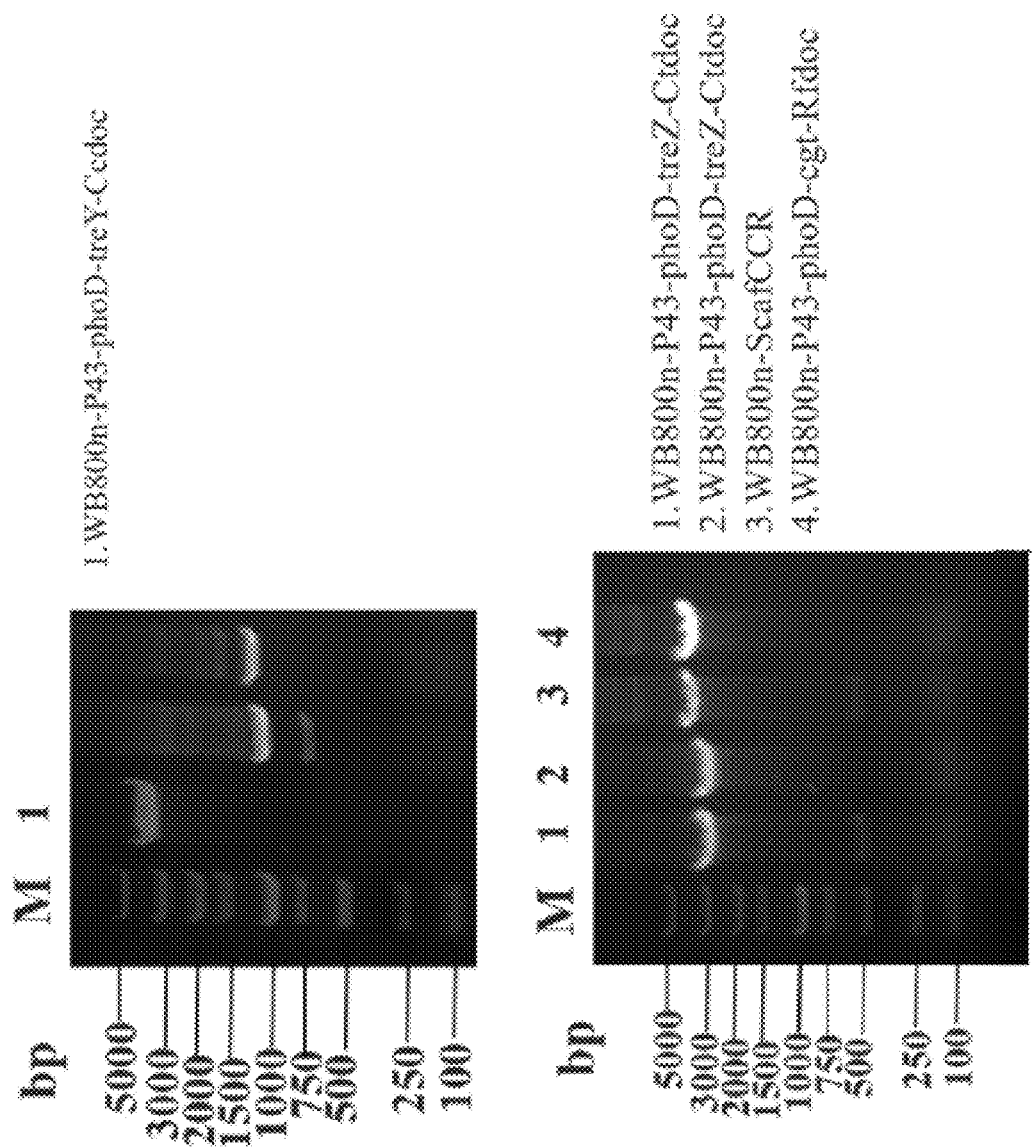
FIG. 7 is a verification electropherogram for transformation of WB800n-ScafCCR, WB800n-P43-phoD-treY-Ccdoc, WB800n-P43-phoD-treZ-Ctdoc, and WB800n-P43-phoD-cgt-Rfdoc.

The colony PCR amplification system was 20 μL in volume and included:

1 μL of upstream primer; 1 μL of downstream primer; 1 μL of template; 10 μL of 2×Phanta® Max Master Mix; 7 μL of ddH2O;

The colony PCR amplification procedure was conducted as follows:

denaturation at 95° C. for 3 min; denaturation at 95° C. for 15 s, annealing at 1 min 10 s, extension at 72° C. for 80 min, 30 cycles; extension at 72° C. for 5 min; and storage at 4° C.;

Agarose gel electrophoresis proved that the exogenous fragment P43-phoD-ScafCCR had been transferred into *Bacillus subtilis* WB800n, which was shown in FIG. 7. The recombinant bacterium was named WB800n-ScafCCR.

Example 2

Construction of Recombinant Bacteria WB800n-P43-phoD-treY-Ccdoc

Preparation of the Gene Fragment treY of Malto-Oligosaccharyl Trehalose Synthase (MTSase) and the Gene Fragment of Ccdoc Primers were designed to amplify the gene fragment of P43 promoter and the gene fragment of phoD signal peptide through PCR, using the genome of *Bacillus subtilis* WB800n as a template. The gene fragment treY of malto-oligosaccharyl trehalose synthase (MTSase) was subject to PCR amplification PCR amplification, using *Sulfolobus acidocaldarius* having an accession number of ATCC 33909 genome as a template. Primers were designed to amplify the gene fragment Ccdoc of dockerin, using Sase2-Ccdoc bacterial culture synthesized by Shanghai Sangon Biotech Company as a template. The gel electrophoresis diagram is shown in FIG. 5.

The primers for PCR of the gene sequence of the P43 promoter were as follows:

```
P43-F (SEQ ID NO: 6):
5'-AGTGAATTCGAGCTCAGCTTCGTG

CATGCAGGCCGG-3'

P43-R (SEQ ID NO: 7):
5'-TCAAAACGACTGTCGTATGCCATAAGCT

TCTGTTATTAATTCTTGTCT-3'
```

The PCR reaction system was as follows:

25 μL of 2×Phanta® Max Master Mix, 2.5 μL of 10 μmol/L upstream primer P43-F, 2.5 μL of 10 μmol/L downstream primer P43-R, 2.5 μL of template, ddH2O made up to 50 μL;

The above PCR reaction was carried out according to the following procedure:

denaturation at 95° C. for 3 min; denaturation at 95° C. for 15 s, annealing at 60° C. for 15 s, extension at 72° C. for 15 s, 30 cycles; extension at 72° C. for 5 min; and storage at 4° C.

The primers for PCR amplification of the gene sequence of the phoD signal peptide of were as follows:

```
phoD-F (SEQ ID NO: 8):
5'-AATAACAGAAGCTTATGGCATACGACAG

TCGTTTTGATGAATG-3' phoD-R (SEQ ID NO: 12):
5'-GGTTGCTGATATCACTACTTCAAA

GGCCCCA-3'
```

The PCR reaction system was as follows:

25 μL of 2×Phanta® Max Master Mix, 2.5 μL of 10 μmol/L upstream primer phoD-F, 2.5 μL of 10 μmol/L downstream primer phoD-R, 2.5 μL of template, ddH2O made up to 50 μL;

The above PCR reaction was carried out according to the following procedure:

denaturation at 95° C. for 3 min; denaturation at 95° C. for 15 s, annealing at 60° C. for 10 s, extension at 72° C. for 15 s, 30 cycles; extension at 72° C. for 5 min; and storage at 4° C.

The primers for PCR of the malto-oligosaccharyl trehalose synthase (MTSase) treY gene sequence were as follows:

```
Sase-F (SEQ ID NO: 13):
5'-GGTTGGGGCCTTTGAAGTAGTGAT

ATCAGCAACCTAC-3'
```

```
Sase-R (SEQ ID NO: 14):
5'-ATCGCCATTAACATCGCCCAGCAGTTTTTCC

GGACCCTGGTCCGGCATTCTAACTAGTATCCTA-3'
```

The PCR reaction system was as follows:

25 μL of 2×Phanta® Max Master Mix, 10 μmol/L upstream primer Sase-F 2.5 μL, 10 μmol/L downstream primer Sase-R 2.5 μL, 2.5 μL of template, ddH2O made up to 50 μL.

The above PCR reaction was carried out according to the following procedure:

denaturation at 95° C. for 3 min; denaturation at 95° C. for 15 s, annealing at 60° C. for 70 s, extension at 72° C. for 15 s, 30 cycles; extension at 72° C. for 5 min; and storage at 4° C.

The primers for PCR of the gene sequence of the dockerin Ccdoc of were as follows:

```
ccdoc-F (SEQ ID NO: 15):
5'-TACTAGTTAGAATGCCGGACCAGGGTCCGGA

AAAACTGCTGGGCGATGTTAATGGCGATGAAACA

G-3' ccdoc-R (SEQ ID NO: 16):
5'-GACTCTAGAGGATCCTTAGTGGTGGTGGTGG

TGGTGTTGAATGCTCAGCAGTGCTTTTTTC-3'
```

The PCR reaction system was as follows:

25 μL of 2×Phanta@ Max Master Mix, 2.5 μL of 10 μmol/L upstream primer Ccdoc-F, 2.5 μL of 10 μmol/L downstream primer Ccdoc-R, 2.5 μL of template, ddH2O made up to 50 μL;

The above PCR reaction was carried out according to the following procedure:

denaturation at 95° C. for 3 min; denaturation at 95° C. for 15 s, annealing at 60° C. for 15 s, extension at 72° C. for 15 s, 30 cycles; extension at 72° C. for 5 min; and storage at 4° C.

(2) double digestion of yeast episomal plasmid pHT01 by ScaI and BamHI

The digestion system for pHT01 plasmid was:

16 μL of plasmid pHT01; 1 μL of ScaI; 1 μL of BamHI; 2.5 μL of 10×buffer; 4.5 L of ddH$_2$O.

Reaction conditions: reaction in a metal bath at 37° C. for 2 h.

The product after double digestion of the plasmid was detected by 1% agarose gel electrophoresis and recovered using a DNA gel recovery kit.

Figure 1:
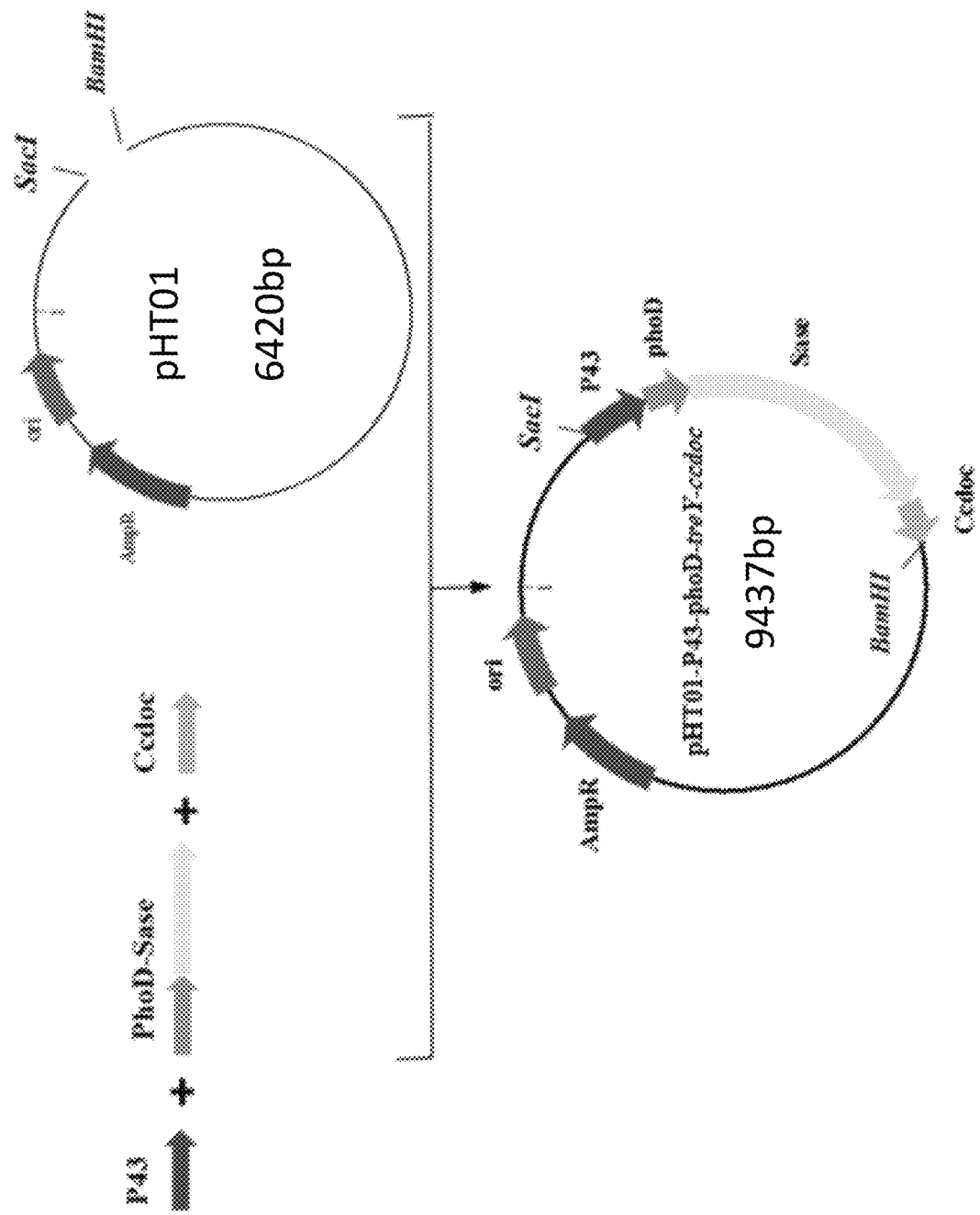
FIG. 1 is a schematic diagram of the construction of vector pHT01-P43-phoD-treY-Ccdoc.

(3) Measurement by Using an Ultra-Light Weight Spectrophotometer (MD2000H):

The gene fragment of the P43 promoter, gene fragment of the phoD signal peptide, gene fragment treY of malto-oligosaccharyl trehalose synthase (MTSase) and gene fragment Ccdoc of dockerin obtained from step (1) and the double digested pHT01 plasmid recovered from step (2) were measured for the concentrations, seamless cloning and ligation of multiple fragments were performed, and the fragments were transformed into E. coli DH5a competent cells. After the identification of successful transformation and sequencing for correctness, the prepared recombinant vector was designated as pHT01-P43-phoD-treY-Ccdoc. After testing, a vector pHT01-P43-phoD-treY-Ccdoc containing a fusion gene consisting of the gene of P43 promoter, the gene of phoD signal peptide, the gene treY of malto-oligosaccharyl trehalose synthase (MTSase) and the gene Ccdoc of dockerin was obtained, and the nucleotide sequence of the gene fragment of P43-phoD-treY-Ccdoc was set forth in SEQ ID NO: 2, and the schematic diagram for vector construction is shown in FIG. 1.

The seamless cloning and ligation system included:

160ng of pHT01 plasmid; 120 ng of P43; 120ng of phoD; 120ng of (MTSase)treY; 120ng of Ccdoc; 2 μL of Exnase; 4 μL of 5×CE buffer; ddH2O made up to 20 μL.

Reaction conditions: reaction in a metal bath at 37° C. for 30 minutes.

The seamless cloning and ligation products were transformed into E. coli DH5α competent cells, and the agarose gel electrophoresis diagram for verification of P43-phoD-treY-Ccdoc was shown in FIG. 6.

(4) Preparation of Electroporation Competent Cells of *Bacillus subtilis* WB800n A single colony of *Bacillus subtilis* WB800n on the surface of fresh LB solid culture medium was picked and placed in 5 mL of LB culture medium and cultured overnight. 1 mL of the overnight culture was inoculated into 50 mL of GM medium (LB+0.5M sorbitol) and cultured with shaking at 37° C. until the OD600 was 1.0. The bacterial culture was placed in an ice-water bath and centrifuged at 5000 rpm for 10 minutes and at 4° C. for 8 minutes. And the bacterial cells were collected. The bacterial cells was re-suspended in 20 mL of pre-cooled ETM culture medium (0.5M sorbitol+0.5M mannitol+10% glycerol), centrifuged at 5000 rpm, 4° C. for 8 min, and the supernatant was removed, and bacterial cells were washed as such 3 times. The washed bacterial cells was re-suspended in 500 μL of ETM culture medium, and dispensed in EP tubes, with 60 μL in each tube.

(5) Transformation of the recombinant plasmid pHT01-P43-phoD-treY-Ccdoc into *Bacillus subtilis* WB800n 5 μL of recombinant plasmid pHT01-P43-phoD-treY-Ccdoc was added to 50 μL competent cells WB800n, incubated on ice for 5 min, added to a pre-chilled electroporation cuvette (2 mm), and electroporation was conducted at 2500V for 5 ms. After the electric shock was finished, 1 mL of RM culture medium (LB+0.5M sorbitol+0.38M mannitol) preheated at 37° C. was added immediately into the electroporation cuvette, shaken and resuscitated at 37° C. for 3h, and spread on the LB plate containing 100 μg/mL of chloramphenicol for inverted culturing at 37° C. to screen for chloramphenicol-resistant strains.

Identification of Medium Containing Positive Recombinant Bacteria WB800n

The above-described positive recombinant bacteria colonies were inoculated into an LB liquid culture medium (containing 100 μg/mL of chloramphenicol) were cultured overnight. Kits from Shanghai Sangon Biotech Company were used to extract the genomic DNA, the obtained genomic DNA was used as a template, and P43-F and Ccdoc-R were used as the primers for PCR amplification.

The colony PCR amplification system was 20 μL in volume and included:

1 μL of upstream primer; 1 μL of downstream primer; 1 μL of template; 10 μL of 2×Phanta® Max Master Mix; 7 μL of ddH$_2$O;

The colony PCR amplification procedure was conducted as follows:

denaturation at 95° C. for 3 min; denaturation at 95° C. for 15 s, annealing at 1 min 35 s, extension at 72° C. for 80 min, 30 cycles; extension at 72° C. for 5 min; and storage at 4° C.;

Agarose gel electrophoresis proved that the exogenous fragment P43-phoD-treY-Ccdoc had been transferred into *Bacillus subtilis* WB800n, which was shown in FIG. 7.

The recombinant bacterium was named WB800n-P43-phoD-treY-Ccdoc.

Example 3

Construction of Recombinant Bacteria WB800n-P43-phoD-treZ-Ctdoc

Preparation of Gene Fragment treZ of Malto-Oligosaccharyl Trehalose Hydrolase (MTHase) and Gene Fragment of Ctdoc Primers were designed to amplify the gene sequence treZ of phoD-malto-oligosaccharyl trehalose hydrolase (MTHase) through PCR, using the genome of *E. coli* strain P43-phoD-MTHase constructed in the laboratory as a template. Primers were designed to amplify the gene fragment Ctdoc of dockerin through PCR, using the Hase2-Ctdoc strain synthesized by Shanghai Sangon Biotech Company as a template. The gel electrophoresis diagram is shown in FIG. 5.

The primers for PCR of the gene sequence phoD-treZ were as follows:

```
F-Hase-phoD (SEQ ID NO: 17):
5'-GAATTAATAACAGAAGCTTATGGCAT

ACGACAGTCGTTTTGATG-3' phoD-Hase-R (SEQ ID NO: 18):
5'-TGCCCGGAACTTTATACGTTTCTAAT

TGATATACCCCAACACCT-3'
```

The PCR reaction system was as follows:

25 µL of 2×Phanta® Max Master Mix, 2.5 µL of 10 µmol/L upstream primer phoD-Hase-F, 2.5 µL of 10 µmol/L downstream primer phoD-Hase-R, 2.5 µL of template, ddH2O made up to 50 µL;

The above PCR reaction was carried out according to the following procedure:

denaturation at 95° C. for 3 min; denaturation at 95° C. for 15 s, annealing at 70° C. for 1 min, extension at 72° C. for 70 s, 30 cycles; extension at 72° C. for 5 min; and storage at 4° C.

After PCR, the length of the fragment was analyzed by 1% agarose gel electrophoresis, the target band was cut based on the size of the fragment, and the gel was recovered using the gel recovery kits from Shanghai Sangon Biotech Company.

The primers for PCR of the gene sequence of dockerin Ctdoc were as follows:

```
ctdoc-F (SEQ ID NO: 19):
5'-GTTGGGGTATATCAATTAGAAACGTATA

AAGTTCCGGGCACACCGA-3' ctdoc-R (SEQ ID NO: 20):
5'-GTCGACTCTAGAGGATCCTTAATGATGA

TGGTGATGATGATTTTT-3'
```

The PCR reaction system was as follows:

25 µL of 2×Phanta® Max Master Mix, 2.5 µL of 10 µmol/L upstream primer ctdoc-F, 2.5 µL of 10 µmol/L downstream primer ctdoc-R, 2.5 µL of template, ddH2O made up to 50 µL;

The above PCR reaction was carried out according to the following procedure:

denaturation at 95° C. for 3 min; denaturation at 95° C. for 15 s, annealing at 60° C. for 15 s, extension at 72° C. for 15 s, 30 cycles; extension at 72° C. for 5 min; and storage at 4° C.

Figure 2:
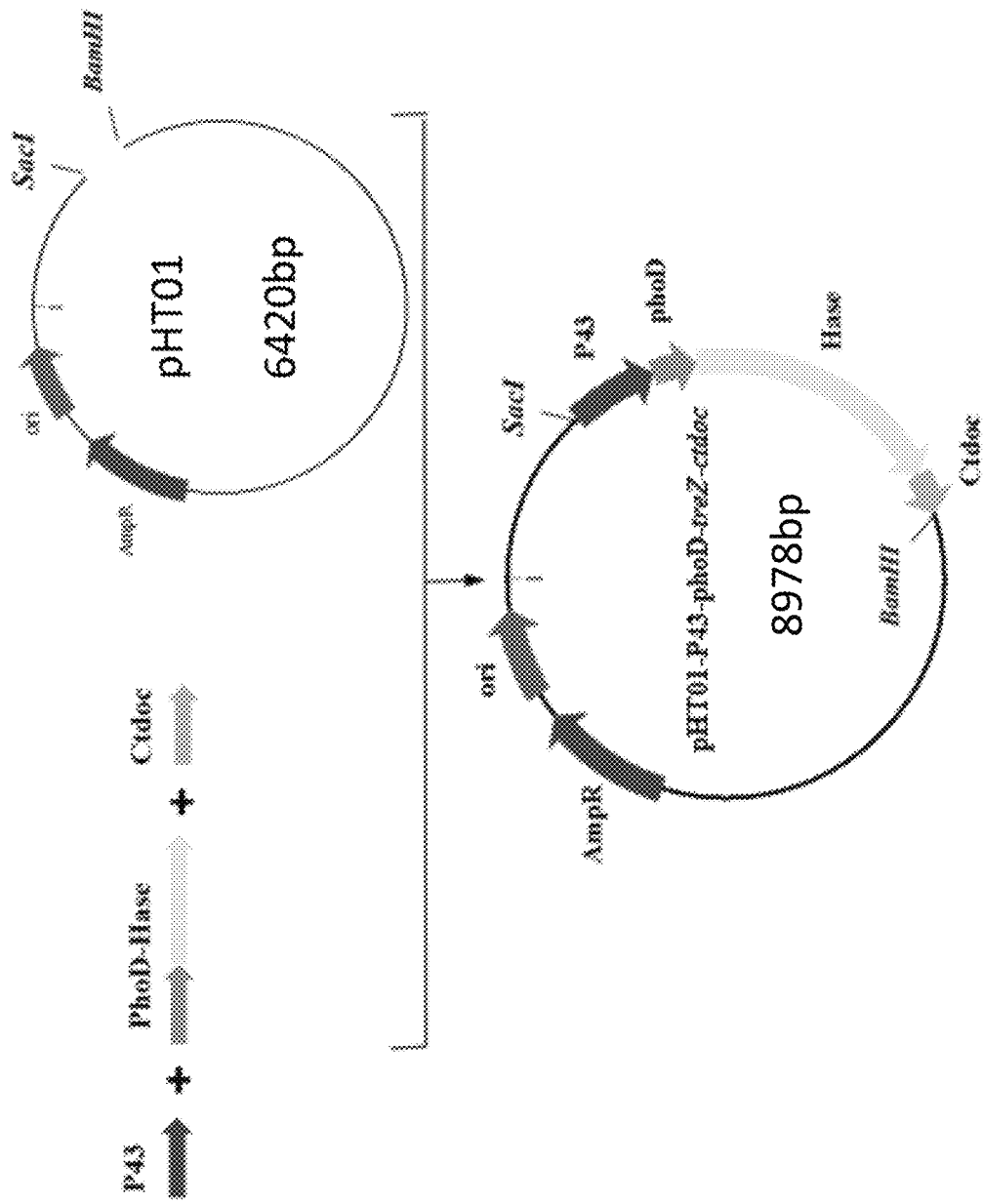
FIG. 2 is a schematic diagram of the construction of vector pHT01-P43-phoD-treZ-ctdoc.

(2) Measurement by Using an Ultra-Light Weight Spectrophotometer (MD2000H):

The gene fragment of the P43 promoter, gene fragment of the phoD signal peptide obtained from Example 2, gene fragment phoD-treZ and gene fragment Ctdoc of dockerin obtained from step 1) and the double digested pHT01 plasmid recovered from step (2) of Example 2 were measured for the concentrations, seamless cloning and ligation of multiple fragments were performed, and the fragments were transformed into *E. coli* DH5α competent cells. After the identification of successful transformation and sequencing for correctness, the prepared recombinant vector was designated as pHT01-P43-phoD-treZ-ctdoc. After testing, a vector pHT01-P43-phoD-treZ-ctdoc containing a fusion gene of the gene of P43 promoter, and the gene phoD-treZ and the gene ctdoc of dockerin was obtained, and the nucleotide sequence of the gene fragment of P43-phoD-treZ-ctdoc was set forth in SEQ ID NO: 3, and the schematic diagram for vector construction is shown in FIG. 2.

The seamless cloning and ligation system included:

160 ng of pHT01 plasmid; 120 ng of P43; 120 ng of phoD-treZ; 120 ng of ctdoc; 2 L of Exnase; 4 µL of 5×CE buffer; ddH2O made up to 20 µL.

Reaction conditions: reaction in a metal bath at 37° C. for 30 minutes.

The seamless cloning and ligation products were transformed into *E. coli* DH5α competent cells, and the gel electrophoresis diagram for verification of P43-phoD-treZ-ctdoc was shown in FIG. 6.

(3) Transformation of the Recombinant Plasmid pHT01-P43-phoD-treZ-Ctdoc into Competent *Bacillus subtilis* WB800n 5 µL of recombinant plasmid pHT01-P43-phoD-treY-Ccdoc was added to 50 µL competent cells WB800n obtained from Example 2, incubated on ice for 5 min, added to a pre-chilled electroporation cuvette (2 mm), and electroporation was conducted at 2500V for 5 ms. After the electric shock was finished, 1 mL of RM culture medium (LB+0.5M sorbitol+0.38M mannitol) preheated at 37° C. was added immediately into the electroporation cuvette, shaken and resuscitated at 37°C for 3h, and spread on the LB plate containing 100 µg/mL of chloramphenicol for inverted culturing at 37° C. to screen for chloramphenicol-resistant strains.

(4) Identification of Medium Containing Positive Recombinant Bacteria WB800n

The above-described positive recombinant bacteria colonies were inoculated into an LB liquid culture medium (containing 100 µg/mL of chloramphenicol) were cultured overnight. Kits from Shanghai Sangon Biotech Company were used to extract the genomic DNA, the obtained genomic DNA was used as a template, and P43-F and Ctdoc-R were used as the primers for PCR amplification.

The colony PCR amplification system was 20 µL in volume and included:

1 µL of upstream primer; 1 µL of downstream primer; 1 µL of template; 10 µL of 2×Phanta® Max Master Mix; 7 µL of ddH2O;

The colony PCR amplification procedure was conducted as follows:

denaturation at 95° C. for 3 min; denaturation at 95° C. for 15 s, annealing at 1 min 20 s, extension at 72° C. for 80 min, 30 cycles; extension at 72° C. for 5 min; and storage at 4° C.;

Agarose gel electrophoresis proved that the exogenous fragment P43-phoD-treZ-ctdoc had been transferred into *Bacillus subtilis* WB800n, which was shown in FIG. 7. The recombinant bacterium was named WB800n-P43-phoD-treZ-Ctdoc.

Example 4

Construction of Recombinant Bacteria WB800n-P43-phoD-Cgt-Rfdoc
Preparation of Glucosyltransferase (CGTase)Cgt-Rfdoc Gene Fragment by Cloning Primers were designed to amplify the gene fragment cgt-rfdoc of glucosyltransferase (CGTase) through PCR, using the bacterial culture of CGTase-rfdoc synthesized by Shanghai Sangon Biotech Company as a template. Primers for reverse PCR amplification of the gene fragment of pHT01-P43-phoD were designed, using the WB800n-P43-phoD-treZ-Ctdoc strain obtained in Example 3 as a template. The gel electrophoresis diagram of the gene fragment cgt-rfdoc is shown in FIG. 5.

The primers for PCR of the glucosyltransferase (CGTase) cgt-Rfdoc gene fragment were as follows:

```
cgt-rfdoc-F (SEQ ID NO: 21):
5'-CGGTTGGGGCCTTTGAAGTAATGGGATCC

GGCGACAG-3' cgt-rfdoc-R (SEQ ID NO: 22):
5'-TCGACTCTAGAGGATCCTTAGTGGTGGTGG

TGGTGGTGCTGAGGAAGTGTGATGAG-3'
```

The PCR reaction system was as follows:

25 μL of 2×Phanta® Max Master Mix, 2.5 μL of 10 μmol/L upstream primer cgt-rfdoc-F, 2.5 μL of 10 μmol/L downstream primer cgt-rfdoc-R, 2.5 μL of template, ddH2O made up to 50 μL.

The above PCR reaction was carried out according to the following procedure:

denaturation at 95° C. for 3 min; denaturation at 95° C. for 15 s, annealing at 62° C. for 15 s, extension at 72° C. for 80 s, 30 cycles; extension at 72° C. for 5 min; and storage at 4° C.

After PCR, the length of the fragment was analyzed by 1% agarose gel electrophoresis, the target band was cut out based the size of the fragment, and the gel was recovered using the gel recovery kit from Shanghai Sangon Biotech Company.

The primers for reverse PCR of the gene fragment of pHT01-P43-phoD were as follows:

```
pHT01-P43-phoD-F (SEQ ID NO: 23):
5'-GCACCACCACCACCACCACTAAGGATCCT

CTAGAGTCGACGT-3' pHT01-P43-phoD-R (SEQ ID NO: 24):
5'-CGCCGGATCCCATTACTTCAAAGGCCCCAACC

GACTGGGCAA-3'
```

The PCR reaction system was as follows:

25 μL of 2×Phanta@ Max Master Mix, 2.5 μL of 10 μmol/L upstream primer pHT01-P43-phoD-F, 2.5 μL of 10 μmol/L downstream primer pHT01-P43-phoD-R, 2.5 μL of template, ddH2O made up to 50 μL.

The above PCR reaction was carried out according to the following procedure:

denaturation at 95° C. for 3 min; denaturation at 95° C. for 15 s, annealing at 62° C. for 15 s, extension at 72° C. for 80 s, 30 cycles; extension at 72° C. for 5 min; and storage at 4° C.

After PCR, the length of the fragment was analyzed by 1% agarose gel electrophoresis, the target band was cut out based on the size of the fragment, and the gel was recovered using a gel recovery kit from Shanghai Sangon Biotech Company.

Figure 3:
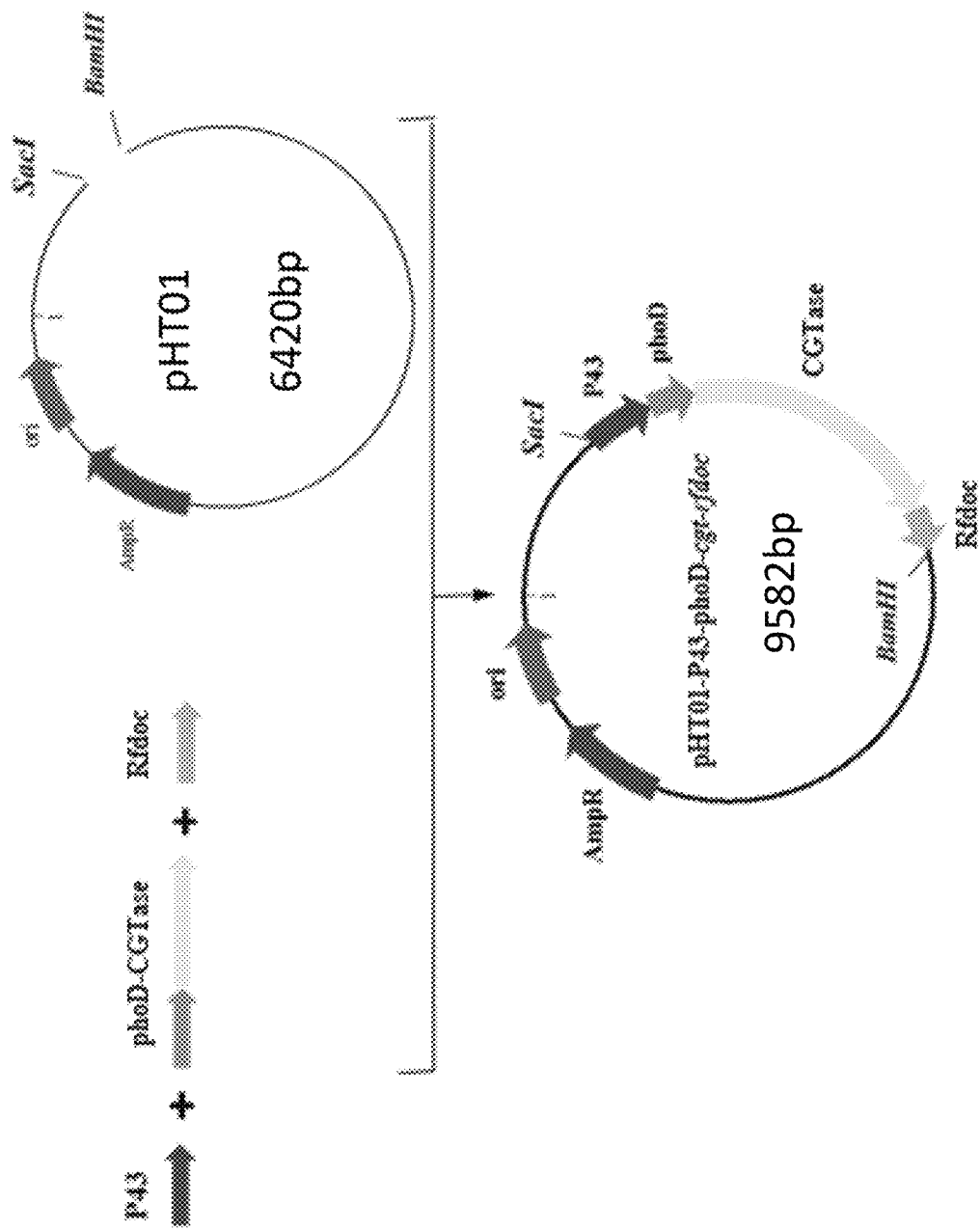
FIG. 3 is a schematic diagram of the construction of vector pHT01-P43-phoD-cgt-rfdoc.

(2) Measurement by Using an Ultra-Light Weight Spectrophotometer (MD2000H):

The gene fragment of the pHT01-P43-phoD promoter, and the gene fragment cgt-rfdoc obtained from step 1) were measured for the concentrations, and seamless cloning and ligation of single fragment were performed, and the fragments were transformed into *E. coli* DH5α competent cells. After the identification of successful transformation and sequencing for correctness, the prepared recombinant vector was designated as pHT01-P43-phoD-cgt-rfdoc. After testing, a vector pHT01-P43-phoD- was obtained, and the nucleotide sequence of the gene fragment of P43-phoD-cgt-rfdoc was set forth in SEQ ID NO: 4, and the schematic diagram for vector construction is shown in FIG. 3.

The seamless cloning and ligation system included:

160 ng of pHT01-P43-phoD fragment; 120 ng of cgt-rfdoc; 2 μL of Exnase; 4 μL of 5×CE buffer; ddH$_2$O made up to 20 μL.

Reaction conditions: reaction in a metal bath at 37° C. for 30 minutes.

The seamless cloning and ligation products were transformed into *E. coli* DH5α competent cells, and the gel electrophoresis diagram for verification of P43-phoD-cgt-rfdoc was shown in FIG. 6.

(3) Transformation of the recombinant plasmid pHT01-P43-phoD-cgt-rfdoc into competent *Bacillus subtilis* WB800n 5 μL of recombinant plasmid pHT01-P43-phoD-cgt-rfdoc was added to 50 μL competent cells WB800n obtained from Example 2, incubated on ice for 5 min, added to a pre-chilled electroporation cuvette (2 mm), and electroporation was conducted at 2500V for 5 ms. After the electric shock was finished, 1 mL of RM culture medium (LB+0.5M sorbitol+ 0.38M mannitol) preheated at 37° C. was added immediately into the electroporation cuvette, shaken and resuscitated at 37° C. for 3 h, and spread on the LB plate containing 100 μg/mL of chloramphenicol for inverted culturing at 37° C. to screen for chloramphenicol-resistant strains.

(4) Identification of Medium Containing Positive Recombinant Bacteria WB800n

The above-described positive recombinant bacteria colonies were inoculated into an LB liquid culture medium (containing 100 μg/mL of chloramphenicol) were cultured overnight. Kits from Shanghai Sangon Biotech Company were used to extract the genomic DNA, the obtained genomic DNA was used as a template, and P43-phoD-F and cgt-rfdoc-R were used as the primers for PCR amplification.

The colony PCR amplification system was 20 μL in volume and included:

1 μL of upstream primer; 1 μL of downstream primer; 1 μL of template; 10 μL of 2×Phanta® Max Master Mix; 7 μL of ddH$_2$O;

The colony PCR amplification procedure was conducted as follows:

denaturation at 95° C. for 3 min; denaturation at 95° C. for 15 s, annealing at 1 min 20 s, extension at 72° C. for 80 min, 30 cycles; extension at 72° C. for 5 min; and storage at 4° C.;

Agarose gel electrophoresis proved that the exogenous fragment P43-phoD-cgt-rfdoc had been transferred into *Bacillus subtilis* WB800n, which was shown in FIG. 7. The recombinant bacterium was named WB800n-P43-phoD-cgt-Rfdoc.

Example 5

Fermentation of positive recombinant Bacteria WB800n-ScafCCR, WB800n-P43-phoD-treY-Ccdoc, WB800n-P43-phoD-treZ-Ctdoc, WB800n-P43-phoD-cgt-Rfdoc Four recombinant Bacteria WB800n-ScafCCR, WB800n-P43-phoD-treY-Ccdoc, WB800n-P43-phoD-treZ-Ctdoc, WB800n-P43-phoD-cgt-Rfdoc as constructed in Examples 1-4 were inoculated into LB solid culture medium and incubated at 37° C. for 12 hours;

the recombinant bacteria in the LB solid culture medium were inoculated into LB liquid culture medium and incubated in thermostatic shaker at 37° C., 200 r/min for 12 h, and an initial seed liquid was prepared;

the seed liquid prepared in step (2) was transferred to a TB liquid medium at a percentage of 1% by volume, and cultivated on a constant-temperature shaker at 37° C., 200 r/min for 10 hours to obtain an inoculated seed liquid;

the inoculated seed liquid prepared in step (3) was transferred to 50 L fermentation medium at a percentage of 10% by volume, and fermented for 48 h at a speed of 500 rpm and, at a temperature of 37° C. The fermentation broth was filtered through a ceramic membrane to obtain a clear fermentation broth from which bacterial cells were removed.

The formula of above culture medium was:

LB solid culture medium: peptone 1 g/L, yeast extract 0.5 g/L, NaCl 1 g/L, agar powder 2 g/L, water balanced;

LB liquid culture medium: peptone 1 g/L, yeast extract 0.5 g/L, NaCl 1 g/L, water balanced, pH 7.0;

TB fermentation medium: tryptone 12 g/L, yeast extract powder 24 g/L, glycerin 4 ml/L, KH$_2$PO$_4$ 2.4 g/L, K$_2$HPO$_4$ 16.5 g/L, water balanced;

Fermentation medium: tryptone 12 g/L, 24 g/L of yeast extract powder, sucrose 12 g/L, KH$_2$PO$_4$ 0.6 g/L, K$_2$HPO$_4$ 4 g/L, water balanced.

Example 6

Recovery of Scaffold Protein by Cellulose Beads

Ionic liquid 1-ethyl-3-methylimidazole acetate ([EMIM]Ac) was used to dissolve cellulose, to prepare a solution having a concentration of 3%. The cellulose was dissolved completely in a constant temperature pot at 80° C., and kept during the dissolution process. Uniform magnetic stirring was performed until a transparent liquid was obtained. Then anhydrous ethanol was used as a coagulation bath to prepare composite microspheres by a squeezing method. Finally, the microspheres were washed 3 times with deionized water to obtain wet cellulose beads. Reference was made to Li Bingjie's master's degree thesis Preparation of Chitosan Cellulose Composite Microspheres and Research on its Adsorption Properties from South China University of Technology when preparing the cellulose beads.

The scaffold proteins in the WB800n-ScafCCR bacteria were recovered by the Cellulose beads through the CBM in the scaffold proteins. The cellulose beads are washed with deionized water and placed in the pure enzyme solution of WB800n-ScafCCR, allowing cellulose beads to adsorb for 3 hours at a constant temperature of 25° C., and cellulose beads were filtered to give the wet recovered scaffold proteins.

Example 7

In Vitro Assembly of Multi-Enzyme Complex

Figure 8:
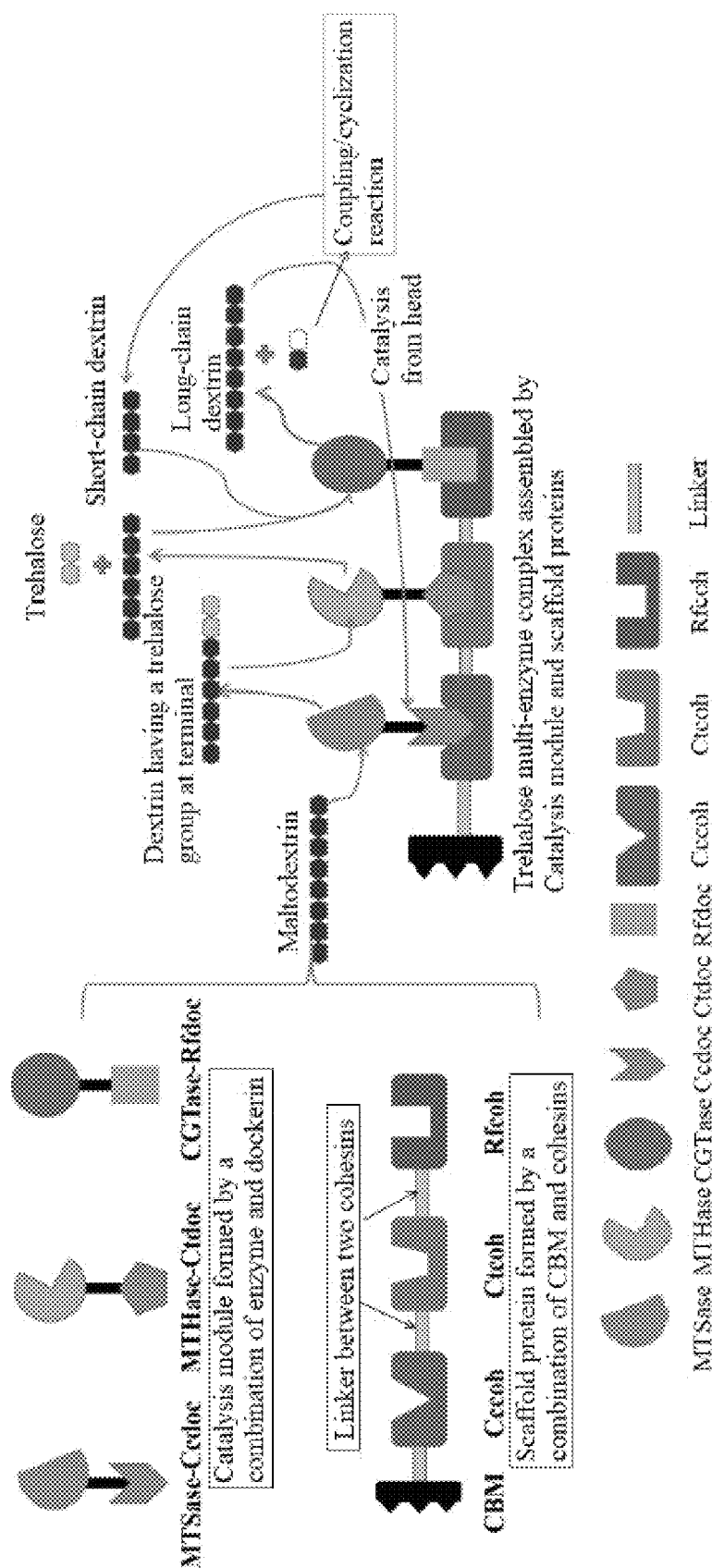
FIG. 8 is a schematic diagram of in vitro assembling of three enzymes with artificial scaffold proteins.

Four positive recombinant bacteria constructed in Example 5 were subjected to secretory expression, and scaffold proteins recovered in Example 6 recovered were mixed in vitro with fusion enzymes MTSase-CcDoc, MTHase-CtDoc and CGTase-RfDoc, this allowed scaffold protein-mediated in vitro assembly of tri-enzyme complex. All of the recombinant MTSase-CcDoc, MTHase-CtDoc and CGTase-RfDoc contained a 6-His tag, and a Ni-Nat affinity chromatography column was used for purification to obtain pure enzyme solution. When assembling the multi-enzyme complex, the ratio of the protein volume of MTSase-CcDoc, MTHase-CtDoc and CGTase-RfDoc was adjusted to 1:1:1, and CaCl$_2$) was added to the reaction solution in a final concentration of up to 10 mM, and reaction solution was incubated at 37° C. for 2 h to form multi-enzyme complex with MTSase:MTHase:CGTase=1:1:1, and the in vitro assembly of the multi-enzyme complex using the cellulose beads was completed. The in vitro assembly of three enzymes with the scaffold protein was shown in FIG. 8.

Example 8

Isolation and Recovery of Trehalose Multi-Enzyme Complex

Figure 9:
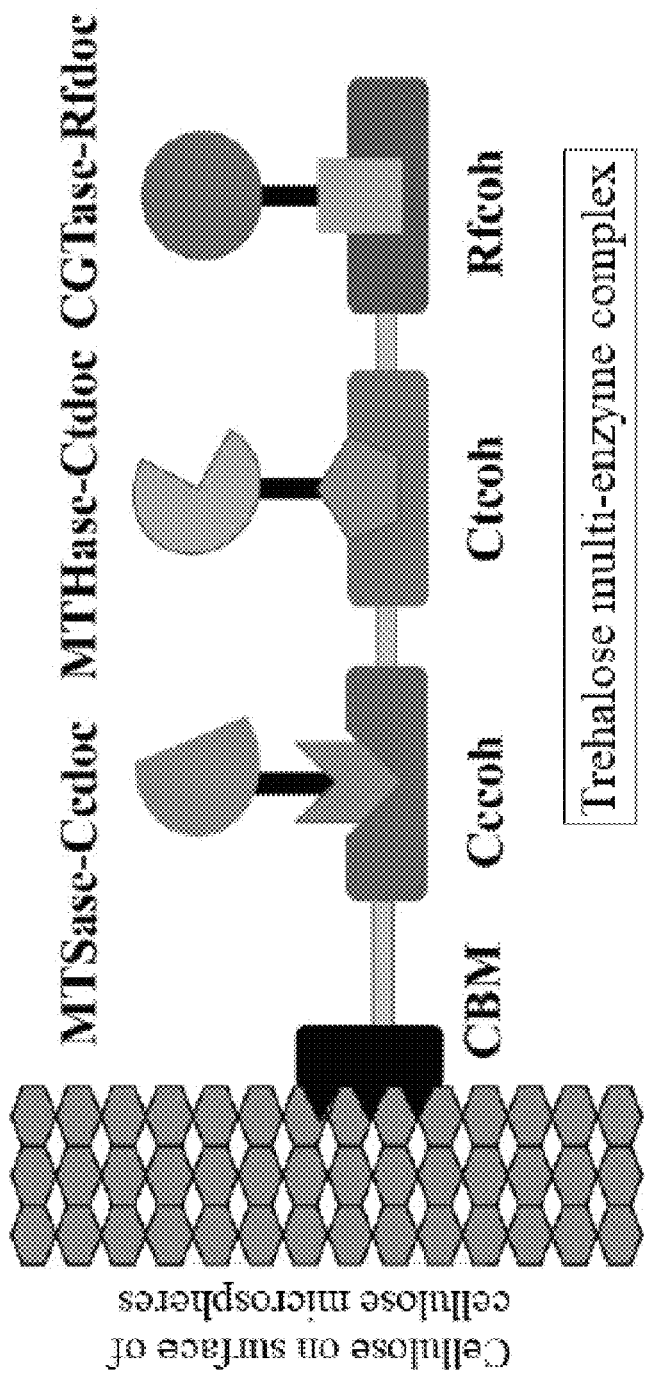
FIG. 9 is a schematic diagram of cellulose beads on whose surface the trehalose multi-enzyme complex are adsorbed and immobilized.

The scaffold proteins prepared in Example 6 by recovery were used to assemble the multi-enzyme complex in vitro in a manner as described in Example 7, and the resulting mixture was filtered and washed. Cellulose beads were recovered and the cellulose beads adsorbed and immobilized trehalose multi-enzyme complex on surface of the cellulose beads, which is schematically shown in FIG. 9.

Comparative Example 1

Three enzymes of Malto-oligosaccharyl trehalose synthase (MTSase), malto-oligosaccharyl trehalose hydrolase (MTHase) and glucosyltransferase (CGTase) were uniquely mixed, and plasmids pHT01-P43-phoD-MTSase, pHT01-P43-phoD-MTHase, and pHT01-P43-phoD-CGTase were likewise constructed using P43 as a promoter and phoD as a signal peptide and the plasmids were separately transformed into *B. subtilis* WB800n bacteria to obtain positive recombinant bacteria which were designated as WB800n-P43-phoD-MTSase, WB800n-P43-phoD-MTHase, and WB800n-P43-phoD-CGTase.

The fermentation method of Example 5 was used to ferment the positive recombinant bacteria, and the positive recombinant bacteria were subjected to secretory expression and mixed in vitro to form a free mixed fermentation broth.

Comparative Example 2

Different numbers of combinations of cohesin gene were designed, and the plasmid pHT01-P43-phoD-Rfcoh-Ctcoh- CBM-Cccoh-Cccoh with a gene sequence of Rfcoh-Ctcoh-CBM-Cccoh-Cccoh for the scaffold protein in the trehalose multi-enzyme complex were transformed into *B. subtilis* WB800n bacteria to obtain positive recombinant bacteria which was designated as WB800n-P43-phoD-Scaf-2.

The fermentation method of Example 5 was used to ferment the positive recombinant bacteria, the positive recombinant bacteria were subjected to secretory expression, and the multi-enzyme complex MTSase-MTHase-CGTase was assembled in vitro to yield a multi-enzyme complex in the fermentation supernatant with a ratio of MTSase:MTHase:CGTase=1:2:1.

Comparative Example 3

The plasmid pHT01-P43-phoD-Rfcoh-Ctcoh-Ctcoh-CBM-Cccoh with a gene sequence of Rfcoh-Ctcoh-Ctcoh-CBM-Cccoh for the scaffold protein in the trehalose multi-enzyme complex was transformed to bacteria *B. subtilis* WB800n to obtain a positive recombinant bacterium which was designated as WB800n-P43-phoD-Scaf-3.

The fermentation method of Example 5 was used to ferment the positive recombinant bacteria, the positive recombinant bacteria were subjected to secretory expression, and the multi-enzyme complex MTSase-MTHase-CGTase was assembled in vitro to yield a multi-enzyme complex in the fermentation supernatant with a ratio of and MTSase:MTHase:CGTase=1:2:1.

Comparative Example 4

The plasmid pHT01-P43-phoD-Rfcoh-Rfcoh-Ctcoh-CBM-Cccoh with a gene sequence of Rfcoh-Rfcoh-Ctcoh-CBM-Cccoh for the scaffold protein in the trehalose multi-enzyme complex was transformed to bacteria *B. subtilis* WB800n to obtain a positive recombinant bacterium which was designated as WB800n-P43-phoD-Scaf-7.

The fermentation method of Example 5 was used to ferment the positive recombinant bacteria, the positive recombinant bacteria were subjected to secretory expression, and the multi-enzyme complex MTSase-MTHase-CGTase was assembled in vitro to yield a multi-enzyme complex in the fermentation supernatant with a ratio of MTSase:MTHase:CGTase=1:1:2.

Comparative Example 5

The plasmid pHT01-P43-phoD-Rfcoh-Rfcoh-Ctcoh-CBM-Cccoh-Cccoh with a gene sequence of Rfcoh-Rfcoh-Ctcoh-CBM-Cccoh-Cccoh for the scaffold protein in the trehalose multi-enzyme complex was transformed to bacteria *B. subtilis* WB800n to obtain a positive recombinant bacterium which was designated as WB800n-P43-phoD-Scaf-5.

The fermentation method of Example 5 was used to ferment the positive recombinant bacteria, the positive recombinant bacteria were subjected to secretory expression, and the multi-enzyme complex MTSase-MTHase-CGTase was assembled in vitro to yield a multi-enzyme complex in the fermentation supernatant with a ratio of MTSase:MTHase:CGTase=3:1:2.

Comparative Example 6

Combinations of cohesin genes of different order were designed, and the plasmid having a scaffold protein gene sequence Cccoh-Ctcoh-Cccoh-Ctcoh-Cccoh-Ctcoh-CBM-Rfcoh was transformed into bacteria *B. subtilis* WB800n to yield a positive recombinant bacterium which was designated as WB800n-P43-phoD-Scaf-6.

The fermentation method of Example 5 was used to ferment the positive recombinant bacteria, the positive recombinant bacteria were subjected to secretory expression, and the MTSase-MTHase-CGTase multi-enzyme complex was assembled in vitro, and MTSase was formed in the fermentation supernatant: MTHase:MTSase:MTHase:MTSase:MTHase: The multi-enzyme complex of the CGTase sequence.

Comparative Example 7

Glucosyltransferase derived from a strain different from *Bacillus Circulans* 251 was designed and utilized, and a gene sequence (Genbank: AY770576) of glucosyltransferase derived from *Bacillus lehensis* G1 strain was used to construct a plasmid P43-phoD-Bscgt-Rfdoc plasmid and the plasmid was transformed into *Bacillus subtilis* WB800n, and recombinant bacterium was designated as WB800n-P43-phoD-Bscgt-rfdoc.

The nucleotide sequence of the gene fragment of P43-phoD-Bscgt-Rfdoc is set forth in SEQ ID NO: 5

The fermentation method of Example 5 was used to ferment the positive recombinant bacteria, the positive recombinant bacteria were subjected to secretory expression, and the multi-enzyme complex MTSase-MTHase-BsCGTase was assembled in vitro to yield a multi-enzyme complex in the fermentation supernatant with a ratio of MTSase:MTHase:CGTase=1:1:1.

Comparative Example 8

Three enzymes of malto-oligosaccharyl trehalose synthase (MTSase), malto-oligosaccharyl trehalose hydrolase (MTHase) and glucosyltransferase (CGTase) were uniquely mixed to determine the enzymetic properties of the combined free enzymes, including optimal action temperature and, optimal pH.

Technical Effect Example

The conversion rates of the multi-enzyme complex formed in Example 7 and in Comparative Examples 1-7 were measured.

Method for measurement: To a fermentation supernatant of multi-enzyme complex form in Example 7 and to a fermentation supernatant of mixed free enzymes in Comparative Example 1-7 were separately added to 20% maltodextrin, and the transformation was carried out at a controlled temperature of 55° C., pH of 5.5, 100 rpm/min of stirring speed. After 8 hours of transformation, 0.1% α-amylase was added to, treat at 55° C. for 12 hours and at 100° C. for 10 minutes to inactivate the enzyme, and the content of trehalose in the reaction solution (saccharified liquid) was measured. Comparison of the conversion rate is shown in Analysis Table 1, Analysis Table 2 and Analysis Table 3.

The method for measurement of trehalose content in the reaction solution included:

The concentration of trehalose produced in the reaction solution (saccharified liquid) was determined by high performance liquid chromatography. During the determination, an amino column was used. The column temperature was 40° C., a mixed solution of acetonitrile and water (volume ratio was 3:1) was used as the mobile phase, the flow rate was 1 mL/min, the detector was a differential detector, and the detection time was 20 min.

Trehalose conversion rate =

$$\frac{\text{Total amount of trehalose in saccharified liquid(g)}}{\text{Total amount of maltodextrin in raw material(g)}} \times 100\%$$

Analysis Table 1

| Test group | Test mode | Conversion rate of trehalose |
|---|---|---|
| Example 7 | MTSase:MTHase:CGTase = 1:1:1 | 62.4% |
| Comparative Example 1 | Mixed free enzymes of MTSase, MTHase, and CGTase | 30.5% |
| Example 6 | MTSase:MTHase:MTSase:MTHase:MTSase:MTHase:CGTase | 74.2% |

Analysis Table 2

| Test group | MTSase:MTHase:CGTase (ratio) | Conversion rate of trehalose |
|---|---|---|
| Example 7 | 1:1:1 | 62.4% |
| Comparative Example 2 | 2:1:1 | 68.3% |
| Comparative Example 3 | 1:2:1 | 62.8% |
| Comparative Example 4 | 1:1:2 | 67.2% |
| Comparative Example 5 | 3:1:2 | 78.3% |

Analysis Table 3

| Test group | MTSase:MTHase:CGTase/BsCGTase (ratio) | Conversion rate of trehalose |
|---|---|---|
| Example 7 | 1:1:1 | 62.4% |
| Comparative Example 7 | 1:1:1 | 60.7% |

Analysis Table 4

| Test group | Optimal pH value | Optimal temperature |
|---|---|---|
| Example 7 | 5.5 | 65° C. |
| Comparative Example 8 | 6.0 | 60° C. |

Result Analysis

It can be seen from the comparison of the trehalose conversion rate in Examples 7 and in Comparative Example 1 that conversion rate for the tri-enzyme complex mediated by the scaffold protein was significantly higher than that for the mixed free enzymes of the three enzymes. In Example 7, in the fermentation supernatant of the positive recombinant bacteria, the conversion rate of the multi-enzyme complex with a ratio of MTSase:MTHase:CGTase=1:1:1 was as high as 62.4%, indicating that the use of this scaffold protein increased the utilization rate of the three enzymes of MTSase, MTHase and CGTase, producing a better catalytic effect and reducing costs.

It can be seen from the comparison of the trehalose conversion rate in Examples 7 and in Comparative Examples 2 and 4 that the conversion rate gradually increased as the MTSase/CGTase ratio increased. In Example 7, in the fermentation supernatant of the positive recombinant bacteria, the conversion rate of the multi-enzyme complex with a ratio of MTSase:MTHase:CGTase=1:1:1 was as high as 62.4%. However, when MTSase:MTHase:CGTase=2:1:1 and MTSase:MTHase:CGTase=1:1:2, the conversion rate was increased to 68.3% and 67.2%, respectively.

In Comparative Example 3, the amount of MTHase enzyme did not increase significantly, which represented only a difference of 0.4% from the conversion rate in Example 7. In Comparative Example 6, the use of MTSase:MTHase:CGTase in different order gave a conversion rate of 74.2%, which was slightly lower than the conversion rate in Comparative Example 5. This was due to the influence of the spatial structure between multiple enzymes on the binding capacity of the substrate. It can be seen from the conversion rate results in Example 7 and in Comparative Examples 2 and 4 that the enzyme addition amount of MTSase and CGTase dictated the conversion rate, which was a limiting factor in the process of multi-enzyme complex conversion and production of trehalose. It can be seen from the conversion rate results in Example 7 and in Comparative Example 7 that glucosyltransferase from different sources had a certain impact on the conversion rate of trehalose. The selected CGTase should match the reaction temperature and pH value for MTSase and MTHase. It can be seen from the results in Example 7 and Comparative Example 8 that the temperature and acid resistance of the multi-enzyme complex of MTSase, MTHase and CGTase was improved after being bound to the scaffold protein. Catalysis reaction proceeded better at an optimal temperature of 65° C., and an optimal pH of 5.5.

The ratio of MTSase determined the conversion rate, which is a limiting factor in the process of multi-enzyme complex conversion and production of trehalose. In the present disclosure scaffold proteins are used as a scaffold to combine MTSase, MTHase and CGTase in the multi-enzyme cascade reaction process through the cohesin-dockerin specific interaction to form an MTSase-MTHase-CGTase multi-enzyme complex with a substrate channel effect. This improves the efficiency of cascade enzyme catalysis, overcomes the problem of low efficiency in multi-enzyme cascade reactions, and provides a new way for industrial production of trehalose. Meanwhile, the cohesin-dockerin specific interaction is a major limiting factor in production of trehalose from multi-enzyme complex mediated by scaffold. Therefore, modifications to linker between the dockerins in the catalytic module and to the linker between the cohesins in the scaffold protein allows to improve the efficiency in the production of trehalose by catalyzing liquefied starch, and this is the key technology to solve the production bottleneck problems.

What is claimed is:

1. A method for constructing a recombinant strain for expressing self-assembled tri-enzyme complex, wherein the method comprises the following steps of:

Step 1: constructing recombinant bacteria WB800n-ScafCCR for self-assembled scaffold protein module, comprising:
(1) designing primers and amplifying a full-length sequence of P43 promoter and a full-length sequence of phoD signal peptide through PCR, using the genome of *Bacillus subtilis* WB800n as a template;
(2) designing primers and amplifying a full-length sequence of Rfcoh-Ctcoh-CBM-Cccoh through PCR, using a ScafCCR gene sequence in a bacterial culture of biosynthetic ScafCCR as a template, and the gene fragment Rfcoh-Ctcoh-CBM-Cccoh is designated as the gene fragment of scaffold protein ScafCCR;
wherein the gene sequence of ScafCCR in the bacterial culture of ScafCCR is formed by ligating cohesins Rfcoh, Ctcoh and Cccoh, as well as a gene sequence of cellulose binding domain (CBD) to plasmid PUC57;
(3) double digesting yeast episomal plasmid pHT01 with restriction endonucleases-ScaI and BamHI;
(4) measuring concentrations of the gene fragment of P43 promoter, the gene fragment of phoD signal peptide obtained in step (1) and the gene fragment of scaffold protein ScafCCR in step (2) and the digested pHT01 plasmid in step (3), then ligating these gene fragments by using a multi-fragment seamless cloning technology, and transforming the ligated fragments into *E. coli* DH5a competent cells, and verifying for successful transformation to obtain a plasmid pHT01-P43-phoD-ScafCCR, wherein the obtained recombinant plasmid is designated as pHT01-ScafCCR;
(5) transforming the recombinant plasmid pHT01-ScafCCR into bacterial cells of *Bacillus subtilis* WB800n to obtain a recombinant bacterium *Bacillus subtilis* WB800n which is designated as WB800n-ScafCCR;

Step 2: constructing recombinant bacteria WB800n-P43-phoD-trey-Ccdoc for self-assembled catalytic module comprising steps of:
a) designing primers for amplifying the gene fragment of P43 promoter and the gene fragment of phoD signal peptide through PCR, using the genome of *Bacillus subtilis* WB800n as a template;
b) amplifying a full-length sequence of treY of malto-oligosaccharyl trehalose synthase (MTSase) through PCR, using the genome of *Sulfolobus acidocaldarius* having a accession number of ATCC 33909 as a template;
c) designing primers and amplifying a gene sequence of dockerin Ccdoc through PCR, using the sequence of Ccdoc in a biosynthetic Ccdoc bacterial culture as a template; wherein in the Ccdoc bacterial culture, the gene sequence of dockerin Ccdoc is ligated to the plasmid PUC57;
d) double digesting the yeast episomal plasmid pHT01 with restriction endonucleases ScaI and BamHI;
e) measuring concentrations of the gene fragment of P43 promoter, the gene fragment of phoD signal peptide obtained in step a), the gene fragment treY of malto-oligosaccharyl trehalose synthase (MTSase) obtained in step b), the gene fragment of dockerin Ccdoc in step c) and the digested pHT01 plasmid in step d), then ligating these fragments by using a multi-fragment seamless cloning technology and transforming the resulting ligated fragments into *E. coli* DH5a competent cells, then verifying for successful transformation of the fragments to obtain a plasmid pHT01-P43-phoD-treY-Ccdoc;
wherein the nucleotide sequence of the gene fragment of P43-phoD-treY-Ccdoc is set forth in SEQ ID NO: 2;
f) transforming the recombinant plasmid pHT01-P43-phoD-treY-Ccdoc obtained in step e) into the genome of the bacterial cells of *Bacillus subtilis* WB800n to obtain a recombinant bacterium *Bacillus subtilis* WB800n which is designated as WB800n-P43-phoD-treY-Ccdoc;

Step 3: constructing recombinant bacteria WB800n-P43-phoD-treZ-Ctdoc for self-assembled catalytic module, comprising steps of:
I) designing primers and amplifying the gene fragment of P43 promoter through PCR, using the genome of *Bacillus subtilis* WB800n as a template,
II) designing primers and amplifying full-length sequence treZ of phoD-malto-oligosaccharyl trehalose hydrolase (MTHase) through PCR to obtain a gene fragment phoD-treZ, using the genome of *E. coli* strain P43-phoD-MTHase constructed according to conventional techniques as a template;
III) designing primers and amplifying a gene sequence of dockerin Ctdoc through PCR, using the sequence of a Ctdoc in a biosynthetic Ctdoc bacterial culture as a template;
wherein in the bacterial culture of Ctdoc, the gene sequence of dockerin Ctdoc is ligated to the plasmid PUC57;
IV) double digesting the yeast episomal plasmid pHT01 with restriction endonucleases ScaI and BamHI;
V) measuring concentrations of the gene fragment of P43 promoter obtained in step I), the gene fragment of phoD-treZ obtained in step II), the gene fragment of dockerin Ctdoc in step III) and the digested pHT01 plasmid in step IV), then ligating these fragments by using a multi-fragment seamless cloning technology and transforming the ligated fragments into *E. coli* DH5a competent cells, and verifying for successful transformation of the fragments to obtain a plasmid pHT01-P43-phoD-treZ-Ctdoc;
wherein the nucleotide sequence of the gene fragment P43-phoD-treZ-Ctdoc is set forth in SEQ ID NO: 3;
VI) transforming the recombinant plasmid pHT01-P43-phoD-treZ-Ctdoc obtained in step V) into bacterial cells of *Bacillus subtilis* WB800n to obtain a recombinant bacterium *Bacillus subtilis* WB800n, and the recombinant bacterium is designated as WB800n-P43-phoD-treZ-Ctdoc;

Step 4: constructing recombinant bacteria WB800n-P43-phoD-cgt-Rfdoc for self-assembled catalytic module, comprising:
i) designing primers and amplifying the gene fragment cgt-Rfdoc of cyclodextrin glycosyltransferase (CGTase)-dockerin Rfdoc through PCR, using the sequence of biosynthetic CGTase-Rfdoc as a template;
wherein CGTase-Rfdoc in the bacterial culture is formed by ligating gene sequences of the cyclodextrin glycosyltransferase (CGTase) and the dockerin Rfdoc to the plasmid PUC57;
ii) designing primers and amplifying the gene fragment of pHT01-P43-phoD through reverse PCR, using the WB800n-P43-phoD-treZ-Ctdoc strain obtained in step 3) as a template,
iii) measuring concentrations of the gene fragment cgt-Rfdoc obtained in step i) and the gene fragment pHT01-P43-phoD obtained in step ii), and ligating these fragments by using a single fragment seamless cloning technique and transforming the ligated fragments into *E. coli* DH5a competent cells, then verifying for successful transformation of the ligated fragments to obtain a plasmid pHT01-P43-phoD-cgt-Rfdoc;
wherein the nucleotide sequence of the gene fragment P43-phoD-cgt-Rfdoc is set forth in SEQ ID NO: 4;
iv) transforming the recombinant plasmid pHT01-P43-phoD-cgt-Rfdoc obtained in step iii) into bacterial cells of *Bacillus subtilis* WB800n to prepared a recombinant bacterium *Bacillus subtilis* WB800n, and the recombinant bacterium is designated as WB800n-P43-phoD-CGT-Rfdoc;

secretorily expressing the recombinant bacterium WB800n-ScafCCR, WB800n-P43-phoD-treY-Ccdoc, WB800n-P43-phoD-treZ-Ctdoc, WB800n-P43-phoD-cgt-Rfdoc as constructed above, and performing self-assembling in vitro to obtain recombinant trehalose multi-enzyme complex;
wherein in substep (2) of Step 1, the nucleotide sequence of the gene fragment of the scaffold protein ScafCCR is set forth in SEQ ID NO: 1.

2. The method according to claim 1, wherein in step (1), nucleotide sequences of primers for PCR amplification of the gene fragment of P43 promoter are P43-F and P43-R and are set forth in SEQ ID NO: 6 and SEQ ID NO: 7, respectively;
nucleotide sequences of primers for PCR amplification of the gene fragment of phoD signal peptide in step (1) are phoD-F and Scaf-phoD-R and are set forth in SEQ ID NO: 8 and SEQ ID NO: 9, respectively; and
in step (2), nucleotide sequences of primers for PCR amplification of the gene fragment of scaffold protein ScafCCR composed of Rfcoh-Ctcoh-CBM-Cccoh are ScafCCR-F and ScafCCR-R and are set forth in SEQ ID NO: 10 and SEQ ID NO: 11, respectively.

3. The method according to claim 1, wherein in step a), nucleotide sequences of primers for PCR amplification of the gene fragment of P43 promoter are P43-F and P43-R and are set forth in SEQ ID NO: 6 and SEQ ID NO: 7, respectively;
in step a), nucleotide sequences of primers for PCR amplification of the gene fragment of phoD signal peptide in step (1) are phoD-F and phoD-R and are set forth in SEQ ID NO: 8 and SEQ ID NO: 12, respectively;
in step b), the nucleotide sequences of primers for PCR amplification of the gene fragment treY of malto-oligosaccharyl trehalose synthase (MTSase) are Sase-F and Sase-R and are set forth in and SEQ ID NO: 13 and SEQ ID NO: 14, respectively; and
in step c), nucleotide sequences of primers for PCR amplification of the gene fragment of dockerin Ctdoc are ccdoc-F and ccdoc-R and are set forth in SEQ ID NO: 15 and SEQ ID NO: 16, respectively.

4. The method according to claim 1, wherein in step I), the nucleotide sequences of primers for PCR amplification of the gene fragment of promoter P43 in step I) are P43-F and P43-R and are set forth in SEQ ID NO: 6 and SEQ ID NO: 7, respectively;
in step II), nucleotide sequences of primers for PCR amplification of the gene fragment of phoD-treZ are phoD-Hase-F and phoD-Hase-R and are set forth in SEQ ID NO: 17 and SEQ ID NO: 18, respectively; and
in step III), nucleotide sequences of primers for PCR amplification of the gene fragment of Ctdoc are ctdoc-F and ctdoc-R and are set forth in SEQ ID NO: 19 and of SEQ ID NO: 20, respectively.

5. The method according to claim 1, wherein in step i), nucleotide sequences of primers for PCR amplification of the gene fragment of cgt-Rfdoc are cgt-rfdoc-F and cgt-rfdoc-R and are set forth in SEQ ID NO: 21 and SEQ ID NO: 22, respectively; and in step ii), nucleotide sequence of primers for PCR amplification of the gene fragment of pHT01-P43-phoD are pHT01-P43-phoD-F and pHT01-P43-phoD-R and are set forth in SEQ ID NO: 23 and SEQ ID NO: 24, respectively.

6. The method according to claim 1, further comprisingof:
(i) subjecting each of engineered strains *Bacillus subtilis* WB800n-P43-phoD-treY-Ccdoc, WB800n-P43-phoD-treZ-Ctdoc, WB800n-P43-phoD-cgt-Rfdoc, WB800n-ScafCCR to activation culturing and scaling-up culturing, respectively, fermenting the strains at 35-38° C. for 40-50h, and using the resulting fermentation broth as a crude enzyme solution;
(ii) recovering the crude enzyme solution of scaffold protein for the strain WB800n-ScafCCR in step (i) by using cellulose beads;
(iii) mixing the crude enzyme solution of the scaffold protein recovered in step (ii) with crude enzyme solutions of the strains WB800n-P43-phoD-treY-Ccdoc, WB800n-P43-phoD-treZ-Ctdoc, and WB800n-P43-phoD-cgt-Rfdoc from step (i) at 30-70° C. and pH 4.0-8.0;
(iv) separating the cellulose beads from the resulting mixed solution in step (iii) by filtration, washing the cellulose beads thoroughly and recovering the cellulose beads after drying;
(v) using the cellulose beads prepared in step (iv) to prepare trehalose through catalysis.

7. The method according to claim 6, wherein in step (i), the activation culturing is conducted for 12 hours under the conditions of 35° C.-38° C., 180-220 rpm, and the medium used in the activation culturing is an LB liquid culture medium.

8. The method according to claim 6, wherein in step (i), the scale-up culturing is conducted for 12 hours under the conditions of 35° C.-38° C., 180-220 rpm, and the culture medium used in the scale-up culturing is a TB culture medium comprising the following components:
15 mL/L of glycerol, 12 g/L of tryptone, 24 g/L of yeast extract powder, 2.5 g/L of $MgCl_2$, 17 mM of $KH_2PO_4$, and 72 mM of $K_2HPO_4$.

9. The method according to claim 6, wherein in step (iv), the drying is conducted under the conditions of a cold trap temperature of −54° C. and a vacuum degree of 8 Pa.

10. A method for producing trehalose by using the recombinant bacteria self-assembled tri-enzyme complex constructed by the method according to claim 2 comprising steps of:
(i) subjecting each of engineered strains *Bacillus subtilis* WB800n-P43-phoD-treY-Ccdoc, WB800n-P43-phoD-treZ-Ctdoc, WB800n-P43-phoD-cgt-Rfdoc, WB800n-ScafCCR to activation culturing and scaling-up culturing, respectively, fermenting the strains at 35-38° C. for 40-50h, and using the resulting fermentation broth as a crude enzyme solution;
(ii) recovering the crude enzyme solution of scaffold protein for the strain WB800n-ScafCCR in step (i) by using cellulose beads;
(iii) mixing the crude enzyme solution of the scaffold protein recovered in step (ii) with crude enzyme solutions of the strains WB800n-P43-phoD-treY-Ccdoc, WB800n-P43-phoD-treZ-Ctdoc, and WB800n-P43-phoD-cgt-Rfdoc from step (i) at 30-70° C. and pH 4.0-8.0;
(iv) separating the cellulose beads from the resulting mixed solution in step (iii) by filtration, washing the cellulose beads thoroughly and recovering the cellulose beads after drying;
(v) using the cellulose beads prepared in step (iv) to prepare trehalose through catalysis.

11. A method for producing trehalose by using the recombinant bacteria self-assembled tri-enzyme complex constructed by the method according to claim 3 comprising steps of:
(i) subjecting each of engineered strains *Bacillus subtilis* WB800n-P43-phoD-treY-Ccdoc, WB800n-P43-phoD-treZ-Ctdoc, WB800n-P43-phoD-cgt-Rfdoc, WB800n-ScafCCR to activation culturing and scaling-up culturing, respectively, fermenting the strains at 35-38° C. for 40-50h, and using the resulting fermentation broth as a crude enzyme solution;
(ii) recovering the crude enzyme solution of scaffold protein for the strain WB800n-ScafCCR in step (i) by using cellulose beads;
(iii) mixing the crude enzyme solution of the scaffold protein recovered in step (ii) with crude enzyme solutions of the strains WB800n-P43-phoD-treY-Ccdoc, WB800n-P43-phoD-treZ-Ctdoc, and WB800n-P43-phoD-cgt-Rfdoc from step (i) at 30-70° C. and pH 4.0-8.0;
(iv) separating the cellulose beads from the resulting mixed solution in step (iii) by filtration, washing the cellulose beads thoroughly and recovering the cellulose beads after drying;
(v) using the cellulose beads prepared in step (iv) to prepare trehalose through catalysis.

12. A method for producing trehalose by using the recombinant bacteria self-assembled tri-enzyme complex constructed by the method according to claim 4 comprising steps of:
(i) subjecting each of engineered strains *Bacillus subtilis* WB800n-P43-phoD-treY-Ccdoc, WB800n-P43-phoD-treZ-Ctdoc, WB800n-P43-phoD-cgt-Rfdoc, WB800n-ScafCCR to activation culturing and scaling-up culturing, respectively, fermenting the strains at 35-38° C. for 40-50h, and using the resulting fermentation broth as a crude enzyme solution;
(ii) recovering the crude enzyme solution of scaffold protein for the strain WB800n-ScafCCR in step (i) by using cellulose beads;
(iii) mixing the crude enzyme solution of the scaffold protein recovered in step (ii) with crude enzyme solutions of the strains WB800n-P43-phoD-treY-Ccdoc, WB800n-P43-phoD-treZ-Ctdoc, and WB800n-P43-phoD-cgt-Rfdoc from step (i) at 30-70° C. and pH 4.0-8.0;
(iv) separating the cellulose beads from the resulting mixed solution in step (iii) by filtration, washing the cellulose beads thoroughly and recovering the cellulose beads after drying;
(v) using the cellulose beads prepared in step (iv) to prepare trehalose through catalysis.

13. A method for producing trehalose by using the recombinant bacteria self-assembled tri-enzyme complex constructed by the method according to claim 5 comprising steps of:

(i) subjecting each of engineered strains of *Bacillus subtilis* WB800n-P43-phoD-treY-Ccdoc, WB800n-P43-phoD-treZ-Ctdoc, WB800n-P43-phoD-cgt-Rfdoc, WB800n-ScafCCR to activation culturing and scaling-up culturing, respectively, fermenting the strains at 35-38° C. for 40-50h, and using the resulting fermentation broth as a crude enzyme solution;

(ii) recovering the crude enzyme solution of scaffold protein for the strain WB800n-ScafCCR in step (i) by using cellulose beads;

(iii) mixing the crude enzyme solution of the scaffold protein recovered in step (ii) with crude enzyme solutions of the strains WB800n-P43-phoD-treY-Ccdoc, WB800n-P43-phoD-treZ-Ctdoc, and WB800n-P43-phoD-cgt-Rfdoc from step (i) at 30-70° C. and pH 4.0-8.0;

(iv) separating the cellulose beads from the resulting mixed solution in step (iii) by filtration, washing the cellulose beads thoroughly and recovering the cellulose beads after drying;

(v) using the cellulose beads prepared in step (iv) to prepare trehalose through catalysis.

* * * * *